(12) United States Patent
Merlo

(10) Patent No.: US 6,238,124 B1
(45) Date of Patent: May 29, 2001

(54) LOCKING JOINT MECHANISM

(76) Inventor: Werner O. Merlo, 51203 Range Rd. 265, Spruce Grove, Alberta (CA), T7Y 1E7

( * ) Notice: Subject to any disclaimer, the term of this patent is extended or adjusted under 35 U.S.C. 154(b) by 0 days.

(21) Appl. No.: 09/229,443

(22) Filed: Jan. 13, 1999

(51) Int. Cl.$^7$ .................................................. F16C 11/06
(52) U.S. Cl. .............................. 403/93; 403/90; 403/96; 403/103
(58) Field of Search ............................... 403/103, 90, 83, 403/84, 92, 93, 94, 96, 98, 102, 107, 116, 324, 325, 330; 248/516

(56) References Cited

U.S. PATENT DOCUMENTS

| | | | |
|---|---|---|---|
| 567,243 | * 9/1896 | Kingsland | 403/84 |
| 675,106 | * 5/1901 | Oberle | 403/90 |
| 1,317,903 | * 10/1919 | Whimster | 403/90 |
| 2,063,504 | * 12/1936 | Horwitt et al. | 403/83 X |
| 2,859,059 | * 11/1958 | Loach et al. | 403/103 |
| 3,433,510 | * 3/1969 | Hulterstrum | 403/90 X |
| 3,691,788 | * 9/1972 | Mazziotti | 403/90 X |
| 3,841,769 | * 10/1974 | Bowerman | 403/90 |
| 4,620,813 | * 11/1986 | Lacher | 403/93 X |
| 5,280,871 | * 1/1994 | Chuang | 403/90 X |
| 5,588,767 | 12/1996 | Merlo . | |
| 5,689,999 | * 11/1997 | Wiley et al. | 403/107 |
| 5,713,633 | * 2/1998 | Lu | 403/93 X |

FOREIGN PATENT DOCUMENTS

291547 * 6/1928 (GB) ...................................... 403/90

* cited by examiner

Primary Examiner—B. Dayoan
Assistant Examiner—David E. Bochna
(74) Attorney, Agent, or Firm—Terry M Gernstein

(57) ABSTRACT

The locking joint mechanism disclosed in U.S. Pat. No. 5,588,767 is improved by including elements that prevent roll of one joint member relative to another joint member. The roll preventing elements include at least one actuator head or pin spaced from another actuator head or pin and which is received in a concavity defined between adjacent protuberances. Various protuberance patterns and overall operating mechanisms are also disclosed.

14 Claims, 28 Drawing Sheets

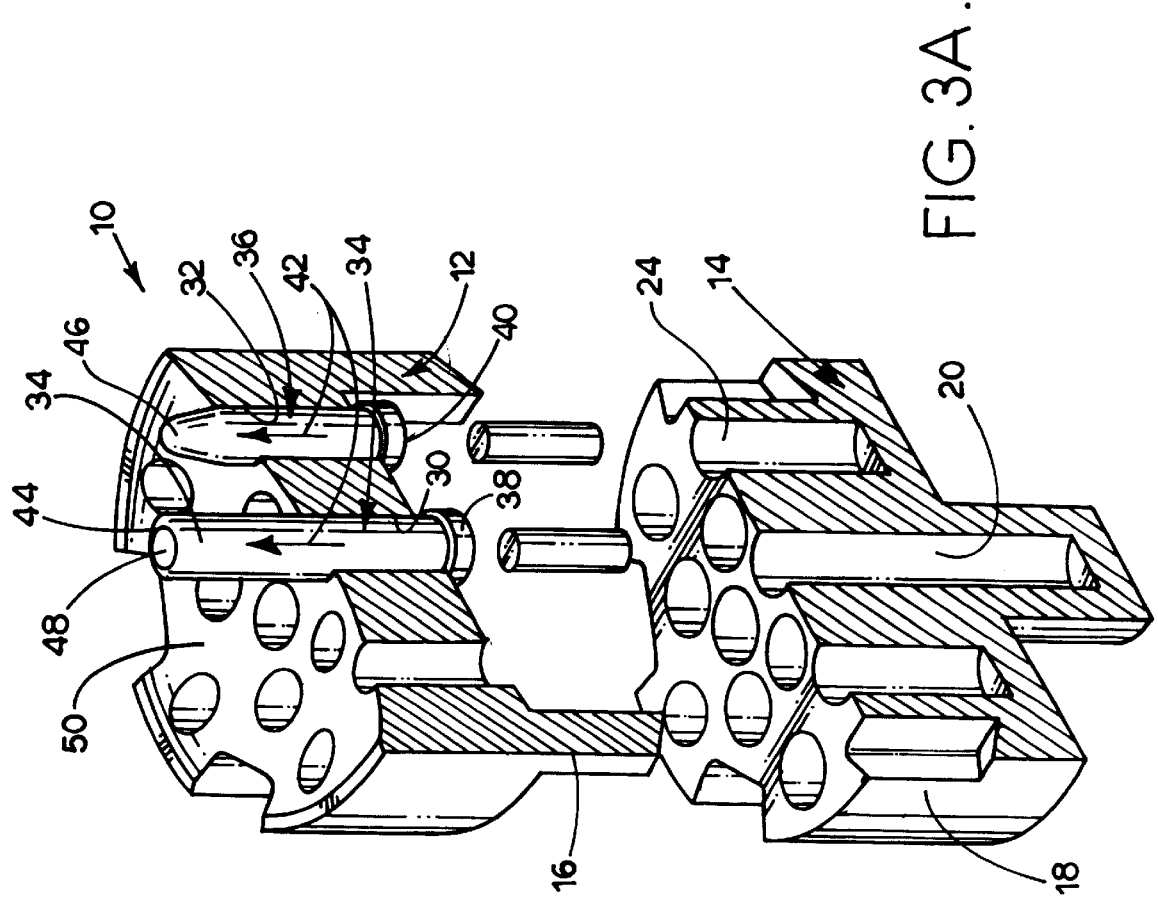

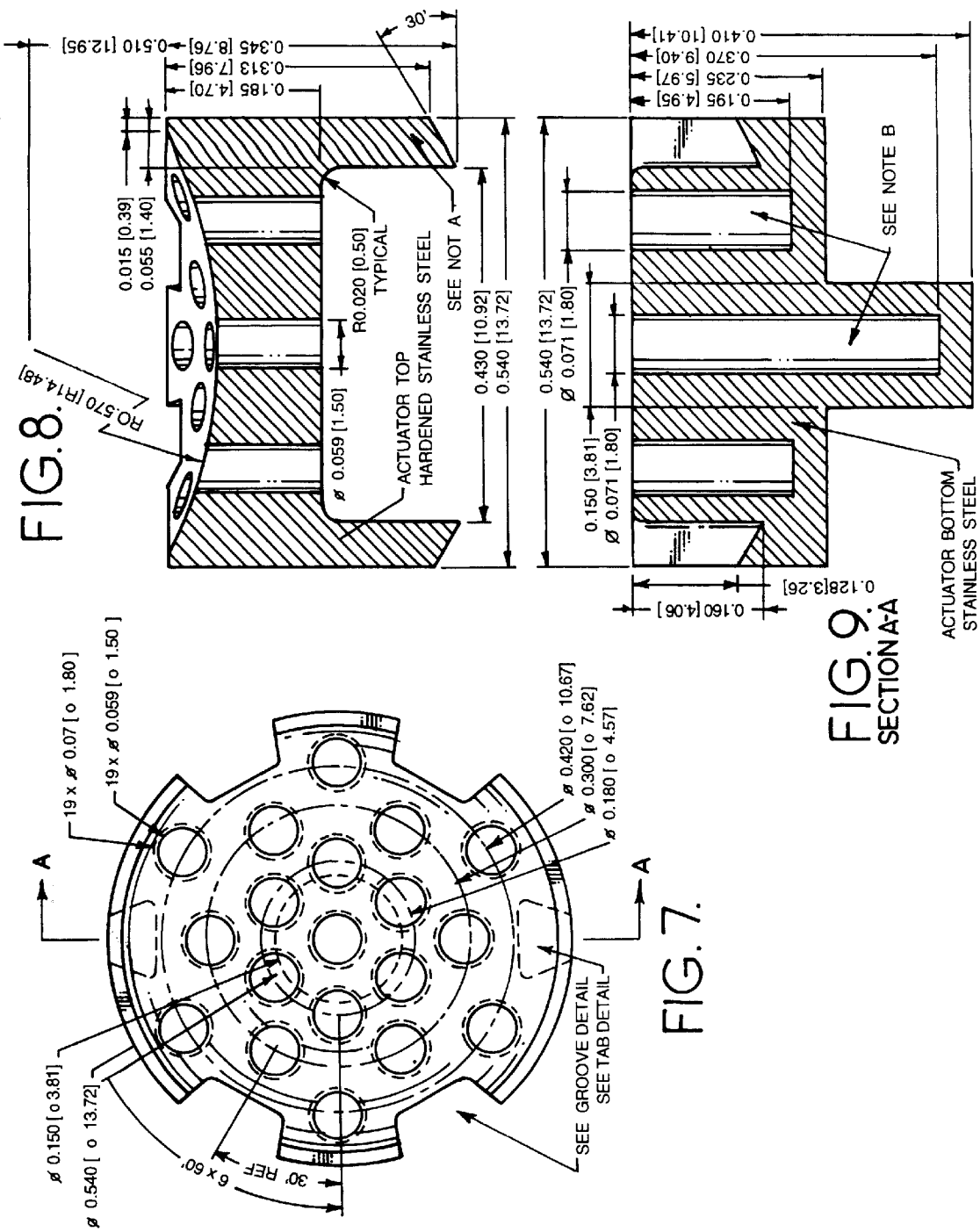

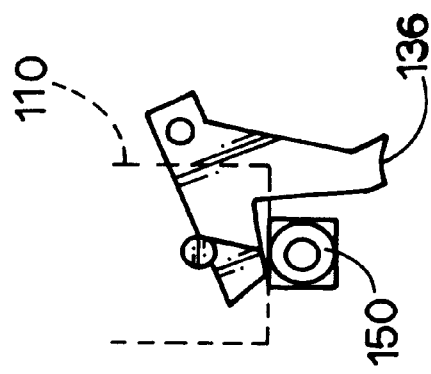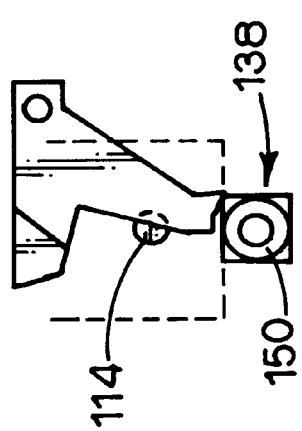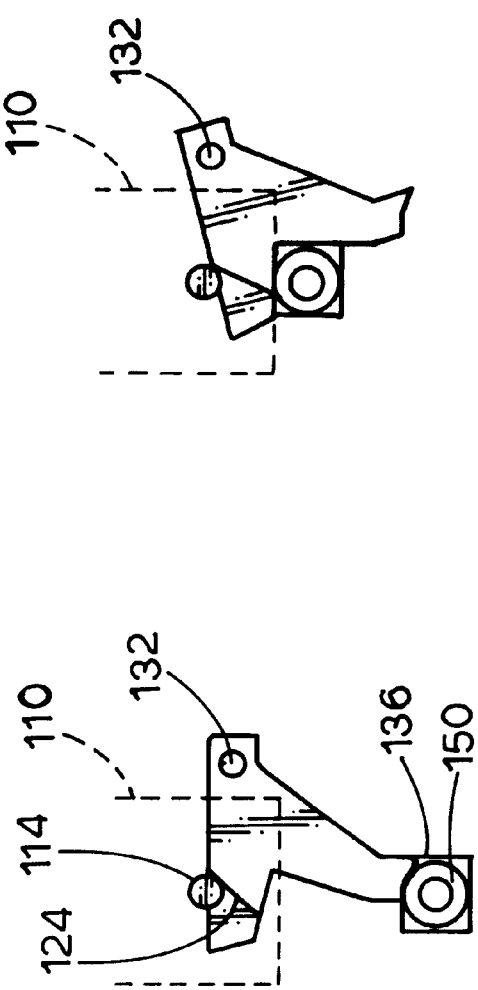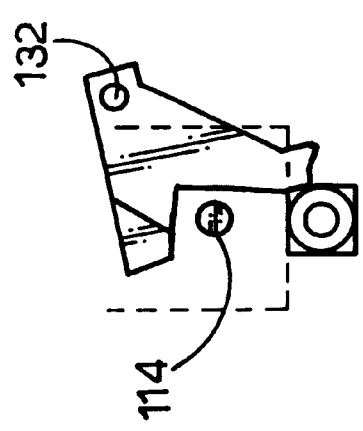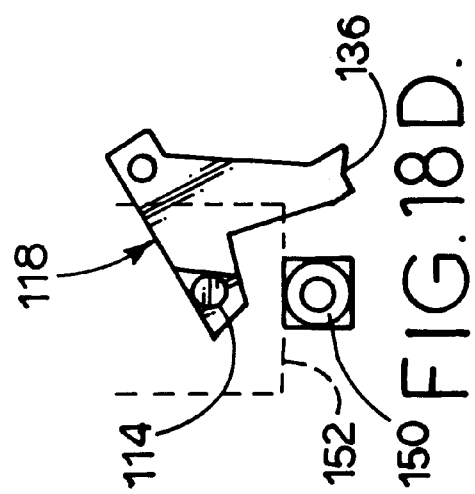

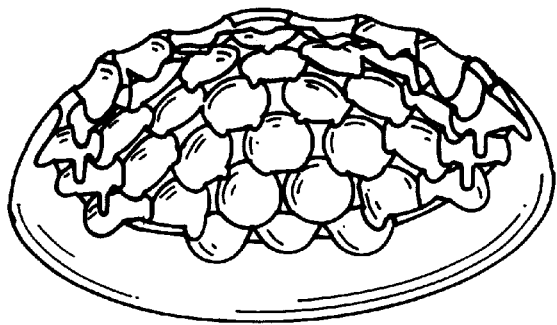
FIG.19A.
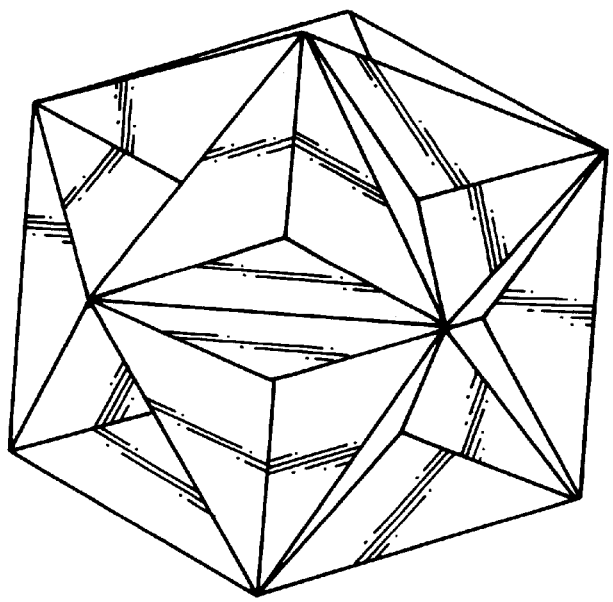
FIG.19E.
FIG.19C.
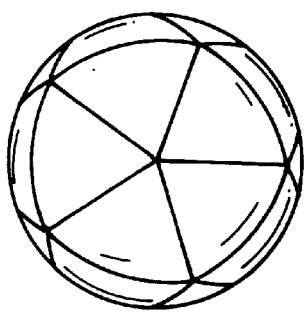

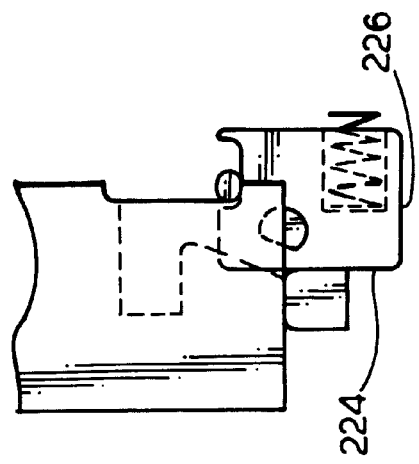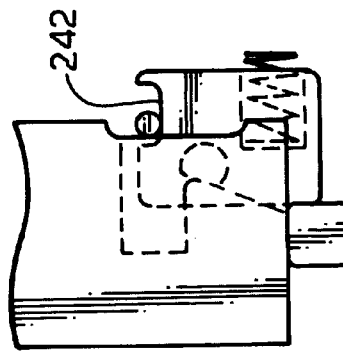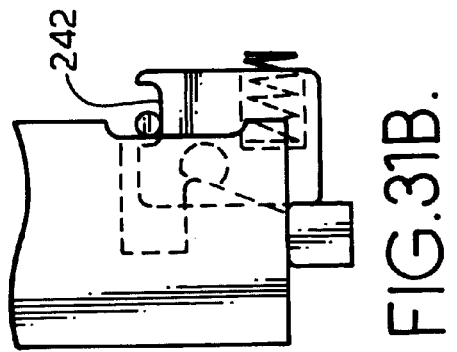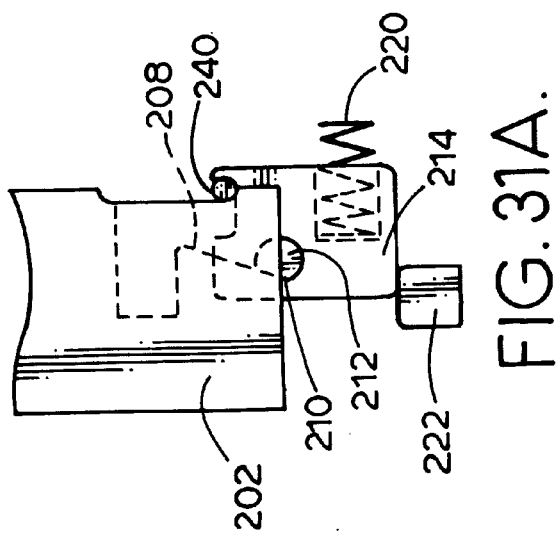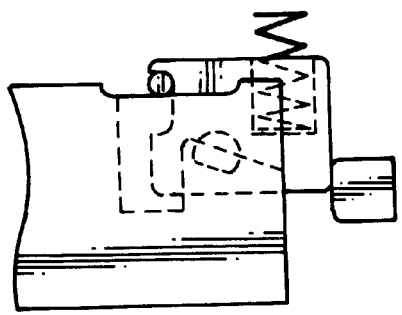

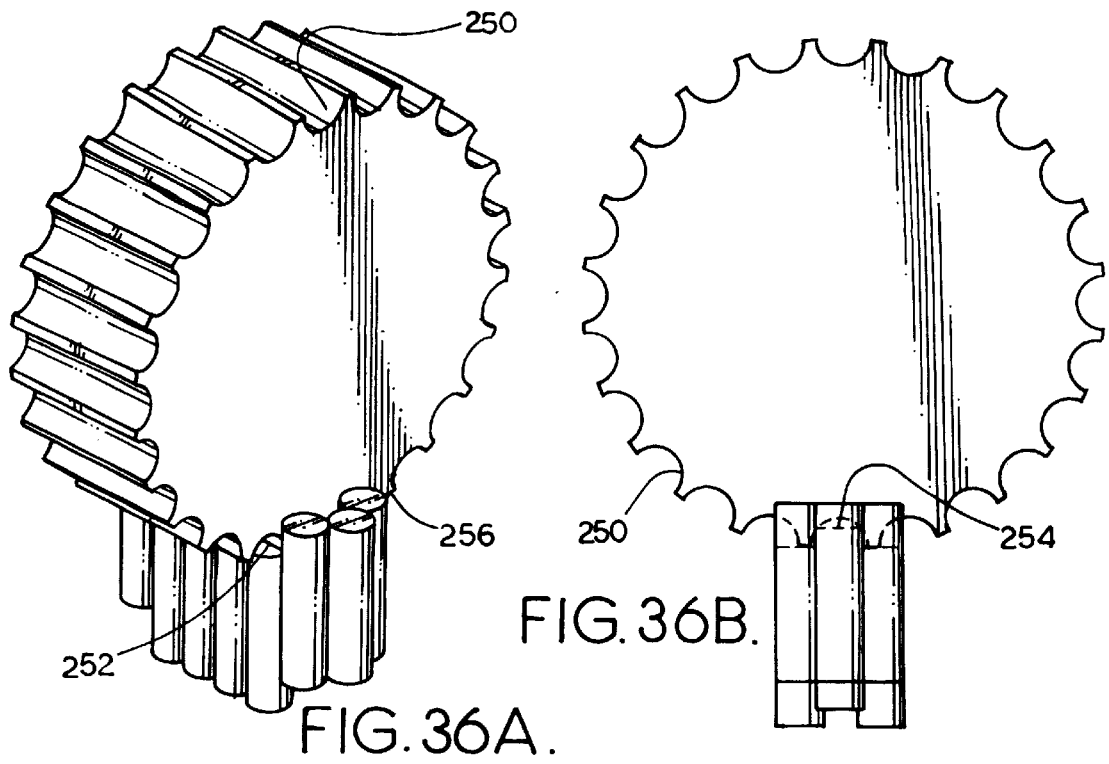
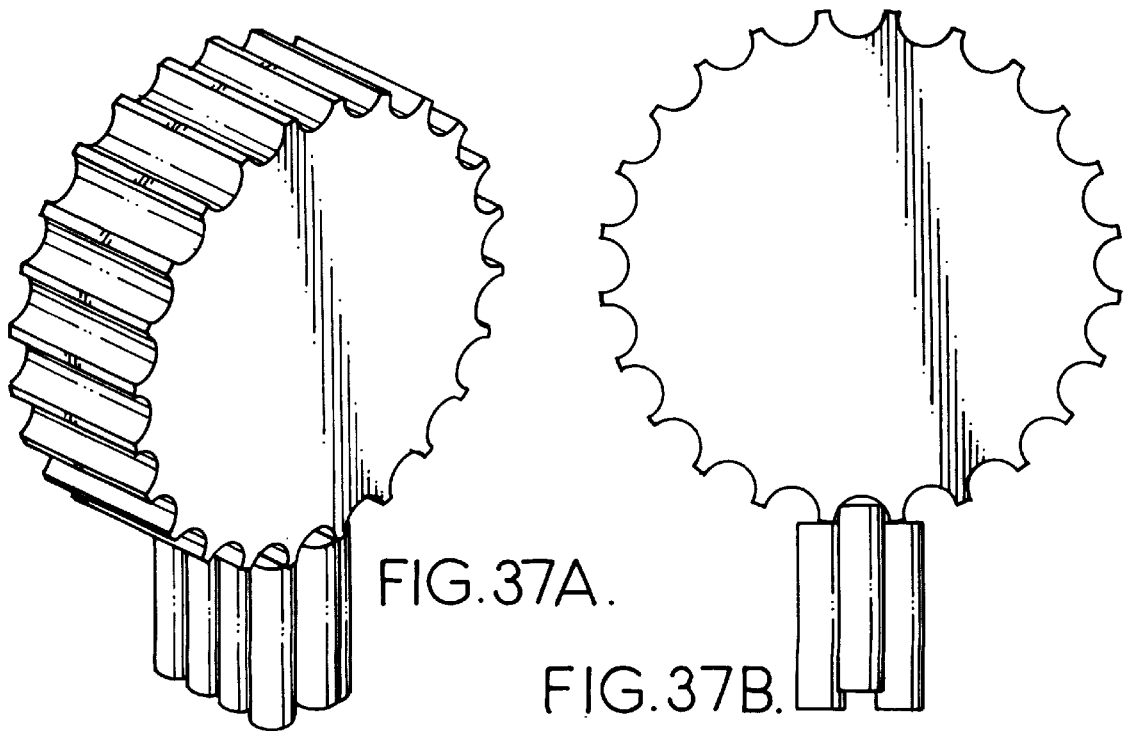

LOCKING JOINT MECHANISM

TECHNICAL FIELD OF THE INVENTION

The present invention relates to the general art of joint mechanisms, and, more particularly, to an improvement in the locking joint mechanism disclosed in U.S. Pat. No. 5,588,767.

BACKGROUND OF THE INVENTION

The present invention is an improvement to the locking joint mechanism disclosed in U.S. Pat. No. 5,588,767, the disclosure of which is fully incorporated herein by reference.

As discussed in the incorporated patent, angularly adjustable, releasably locakable ball joints are used in a variety of assemblies. Such assemblies include umbrellas as well as other jointed items. However, these joint mechanisms are also useful in the field of prosthetics. As discussed in the incorporated patent, it is important for the joint to securely lock two elements together, yet be expeditiously angularly adjustable and releasable when desired.

The locking joint mechanism disclosed in the incorporated patent quite effectively secures the parts against pitch and/or yaw movements between the parts jointed by the mechanism. The inventor has found that the patented joint mechanism can be improved by further securing the joint mechanism against roll movements between the parts joined thereby. This will further improve its performance in many applications, including prosthetics.

Therefore, there is a need to improve the joint mechanism disclosed in U.S. Pat. No. 5,558,767 by further securing the mechanism against roll movements between the parts joined by the joint mechanism.

Still further, while the joint mechanism disclosed in the incorporated patent provides a wide range of adjustments, the inventor has also found that such a joint mechanism can be further improved by providing still greater range of adjustments which is also capable of even finer adjustment steps whereby the relative orientation between the parts joined by the mechanism can be adjusted in extremely fine steps over a wide range.

Therefore, there is a need to improve the joint mechanism disclosed in U.S. Pat. No. 5,588,767 by providing an ability to adjust the relative orientation between the parts joined by the mechanism over a wide range yet in fine incremental steps.

OBJECTS OF THE INVENTION

It is a main object of the present invention to improve the joint mechanism disclosed in U.S. Pat. No. 5,558,767 by further securing the mechanism against roll movements between the parts joined by the joint mechanism.

It is another object of the present invention to improve the joint mechanism disclosed in U.S. Pat. No. 5,588,767 by providing an ability to adjust the relative orientation between the parts joined by the mechanism over a wide range yet in fine incremental steps.

It is a specific object of the present invention to provide an improved locking joint mechanism that is suitable for use in a prosthetic device.

SUMMARY OF THE INVENTION

These, and other, objects are achieved by improving the locking joint mechanism disclosed in U.S. Pat. No. 5,558,767 by adding at least one pin spaced from the main clicker pin disclosed in that patent.

As disclosed in the incorporated patent, the joint mechanism includes a spherical member on one part and an actuator on another part, with the parts being joined by the mechanism and locked into a chosen relative orientation by the joint. A multiplicity of protuberances are located on the spherical member and the main locking clicker pin or actuator is accommodated between the protuberances to lock the parts into the chosen relative orientation. Pitch and yaw are effectively prevented by such engagement.

The additional pin included in the improved joint embodying the present invention is also received in the spaces between the protuberances but at a location that is spaced from the main locking clicker pin or acutator whereby roll movement between the joined parts is prevented. Roll is effectively blocked by two spaced pins, each one interacting with one protuberance or a concavity between protuberances. Therefore, the locking positions are fixed by the number of concavities and/or protuberances. To achieve minute adjustments (i.e., locking positions), more than two pins are used.

Special protuberance patterns are also used to further improve the patented joint mechanism and these patterns can be derived from polyhedrons.

In this manner, and by using more than two actuator heads or pins, not only is the roll effectively prevented, the number of adjustments between the two parts is increased thereby increasing the range of adjustments possible while also increasing the number of increments possible. The increased number of increments allows finer adjustments to be made between the two parts as compared to the patented joint mechanism.

By increasing the range and number of increments of the adjustment over the patented mechanism, the presently-disclosed joint mechanism is more adaptable to use in a number of fields, including prosthetics than prior mechanisms.

BRIEF DESCRIPTION OF THE DRAWING FIGURES

FIG. 1 is a perspective, partly sectional view of the ball, actuator and connecting housing of the joint mechanism disclosed in U.S. Pat. No. 5,588,767.

FIG. 3A is an exploded perspective view of an alternate form of the actuator assembly shown in FIG. 3 with electro-mechanical elements replacing the springs shown in FIG. 3.

FIG. 7 is a top plan view of the socket portion of the actuator assembly.

FIG. 8 is a side elevational cutaway view of top portion of the socket portion of the actuator assembly.

FIG. 9 is a side elevational cutaway view of the bottom portion of the socket portion of the actuator assembly.

FIGS. 18A–18F illustrate operation of the FIG. 16 portion of the mechanism.

FIGS. 19A–19E illustrate various protuberance patterns that can be used on the mechanism of the present invention.

FIGS. 31A–31E illustrate operation of the FIG. 24 mechanism.

FIGS. 36A and 36B show a bi-directional joint using a single wheel.

FIGS. 37A and 37B show a uni-directional joint using a single wheel.

DETAILED DESCRIPTION OF THE PREFERRED EMBODIMENT OF THE INVENTION

Figure 1:
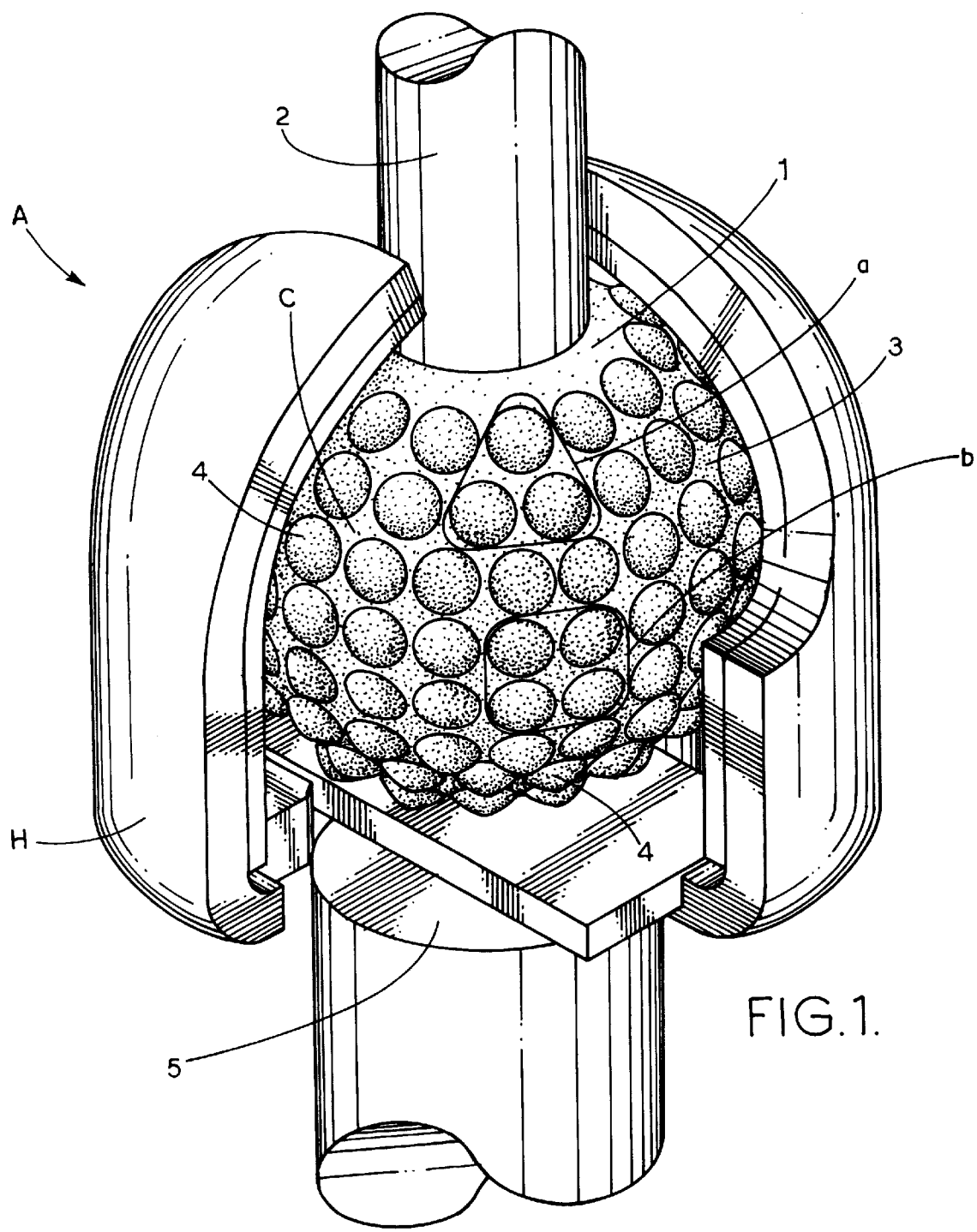
Figure 2:
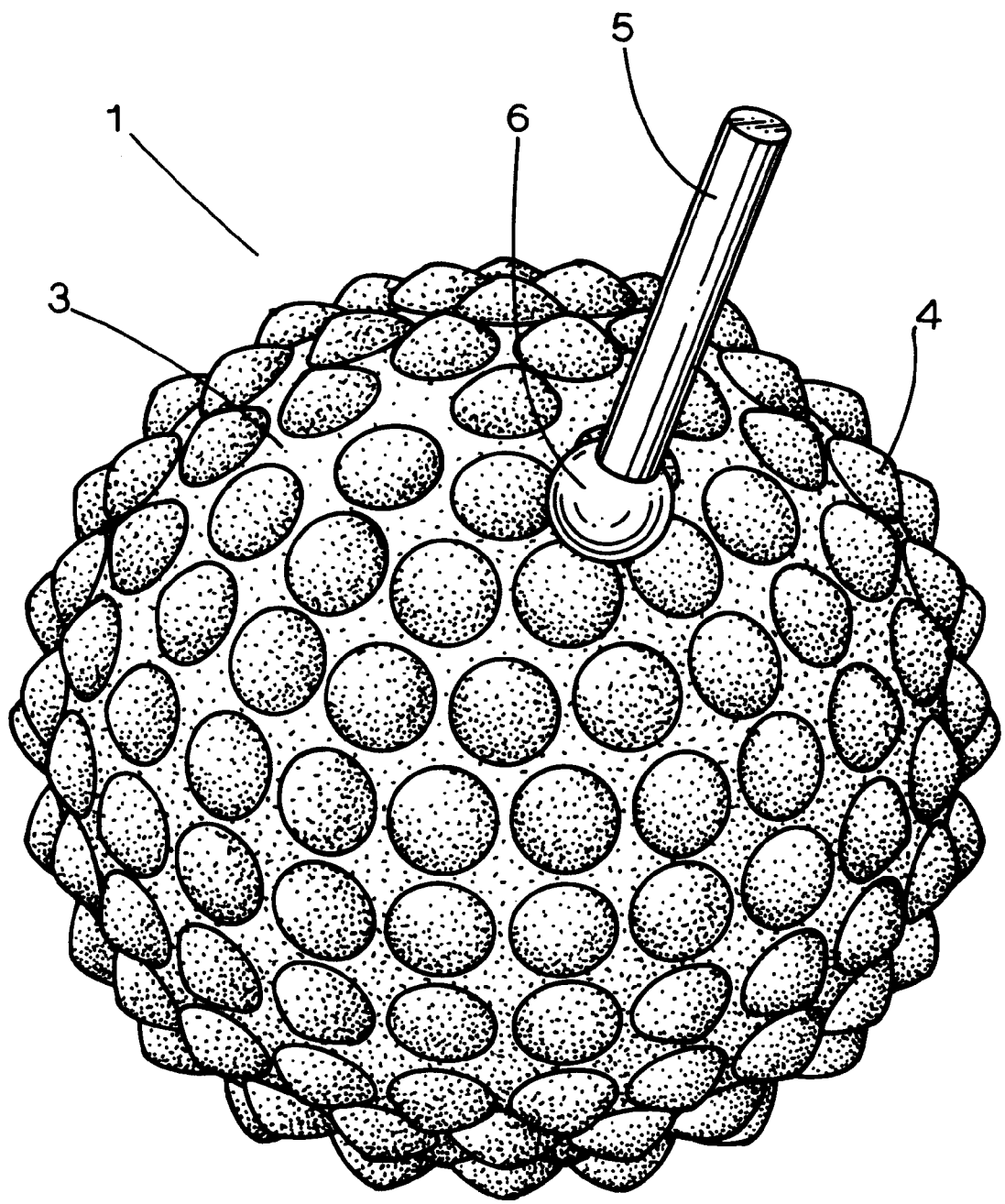
FIG. 2 is a perspective view showing a ball and pin-type actuator in simplified form of the patented mechanism.

Referring first to FIGS. 1 and 2 which illustrate the joint mechanism disclosed in the incorporated patent, a brief description of that joint mechanism will be presented for background purposes.

Joint mechanism A is an angularly adjustable, releasably lockable joint mechanism for rigidly joining first part (not shown) and second part (not shown) at a selected relative orientation. Mechanism A comprises a rounded, or spherical, member 1 connected to a shank 2 which, in turn, is connected to the first part. The spherical member 1 has a plurality of spaces, or concavities C defined on its surface 3 by protuberances 4. Mechanism A further includes a disengageable actuator 5 having a rounded tip 6 and is operative to advance tip 6 toward surface 3 to lock up with rounded member 1 by being located in a concavity C or to retract tip 6 to disengage it from rounded member 1. Actuator 5 is connected with the second part whereby the two parts are joined by mechanism A and functions as a clicker as well as an actuator and as well as a locking member. Mechanism A further includes means, such as housing H, for holding the parts, rounded member 1 and actuator 5 together, with such means being operative to move the actuator out of engagement with the rounded member to allow the parts to change relative orientation when the actuator head is retracted from engagement with the spherical member 1. As shown at a and b in FIG. 1, protuberances 4 on rounded member 1 are arranged in a plurality of patterns of spaced-apart protuberances covering at least part of surface 3. As disclosed in the incorporated patent, the patterns can be polygonal, triangular or rectangular or square, but as will be seen below can have other forms as well. The protuberances of each pattern define a spacing therebetween, which is indicated in the patent as a concavity and indicated herein as concavity C. As disclosed in the patent, the patterns and protuberances are consistent in shape, area and size, and the protuberances, actuator tip and patterns are all dimensioned relative to each other so that the tip can be located in the concavity of each pattern and simultaneously contact all of the protuberances of the pattern adjacent thereto with the contact between the actuator and protuberances being located so that the actuator remains spaced from the surface of the rounded member when the tip is located in the cavity whereby the tip and pattern of protuberances lock together without the tip contacting the surface of the rounded member.

Figure 3:
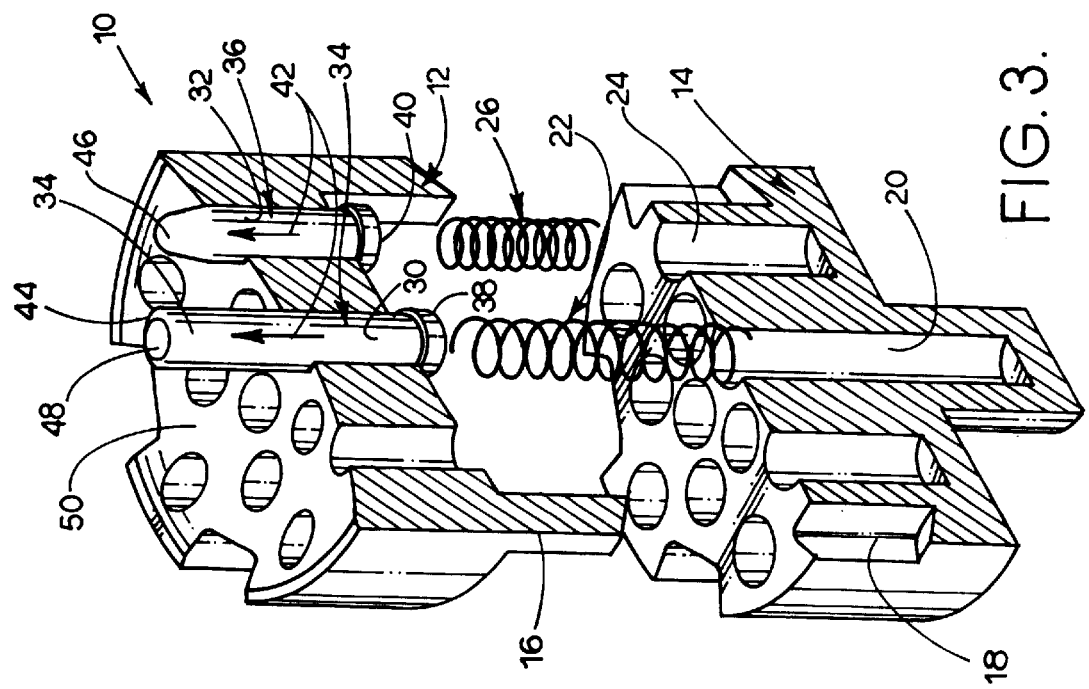
FIG. 3 is an exploded perspective view of the actuator assembly embodying the improvement of the present invention.
Figure 6:
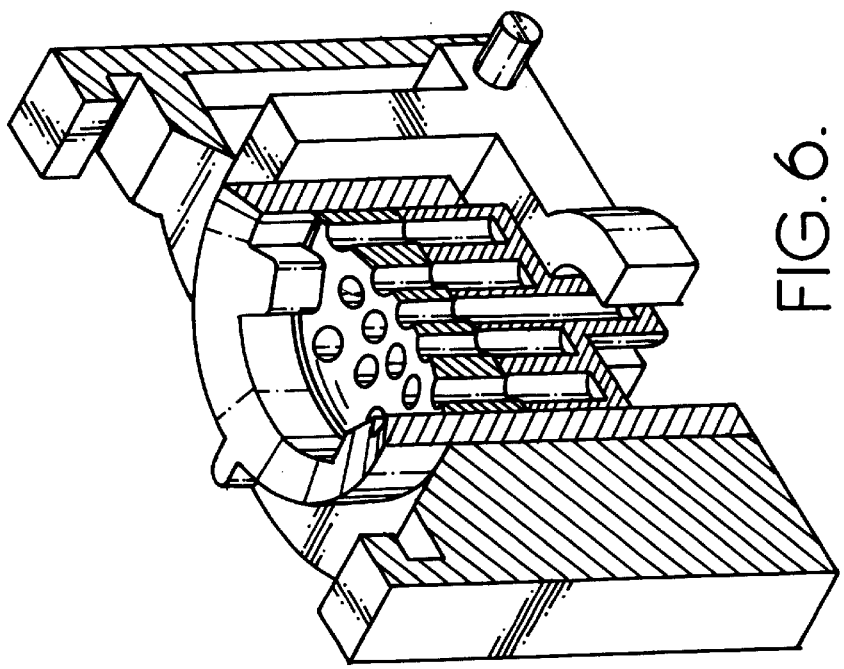
FIG. 6 is a cutaway view of the overall locking mechanism shown in FIG. 5.
Figure 5:
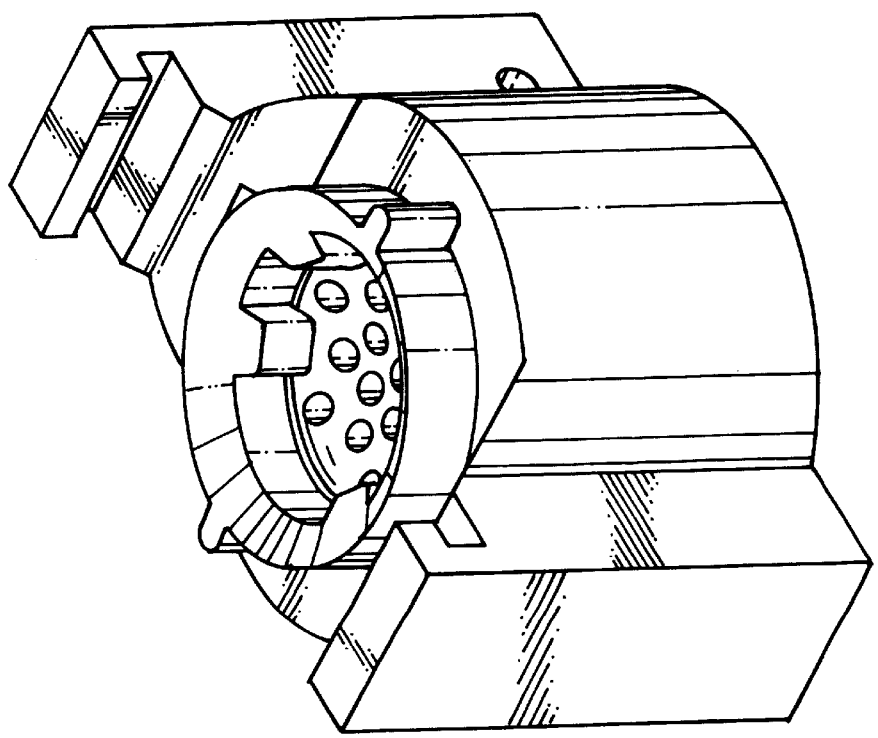
FIG. 5 is an assembled view of the overall locking mechanism of the present invention.
Figure 6A:
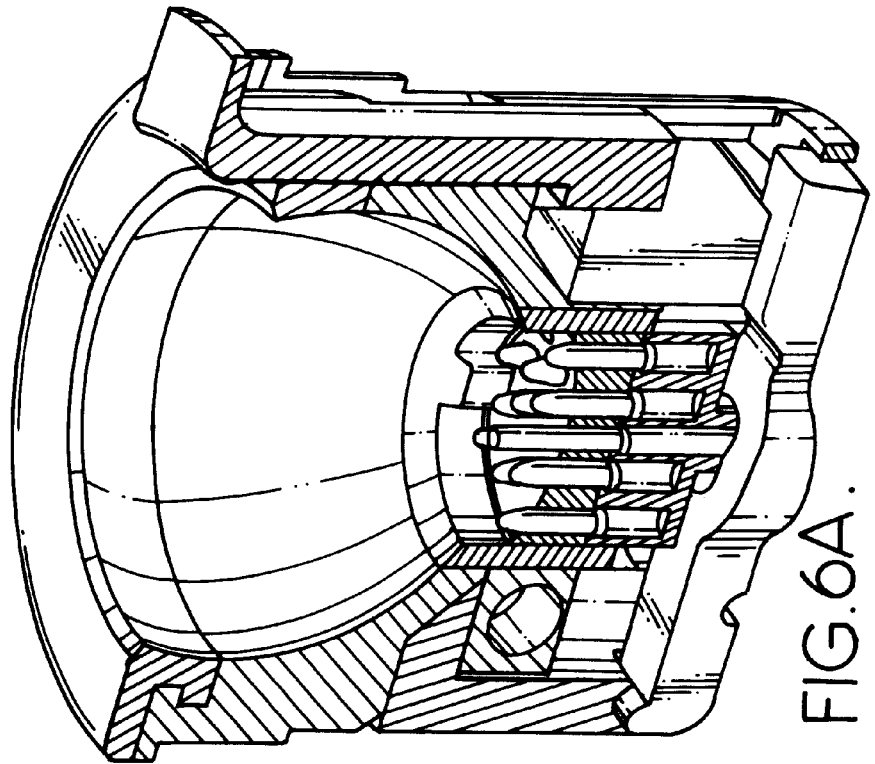
FIGS. 6A and 6B show cutaway views of the overall actuator assemblies shown in FIGS. 5A and 5B.
Figure 5A:
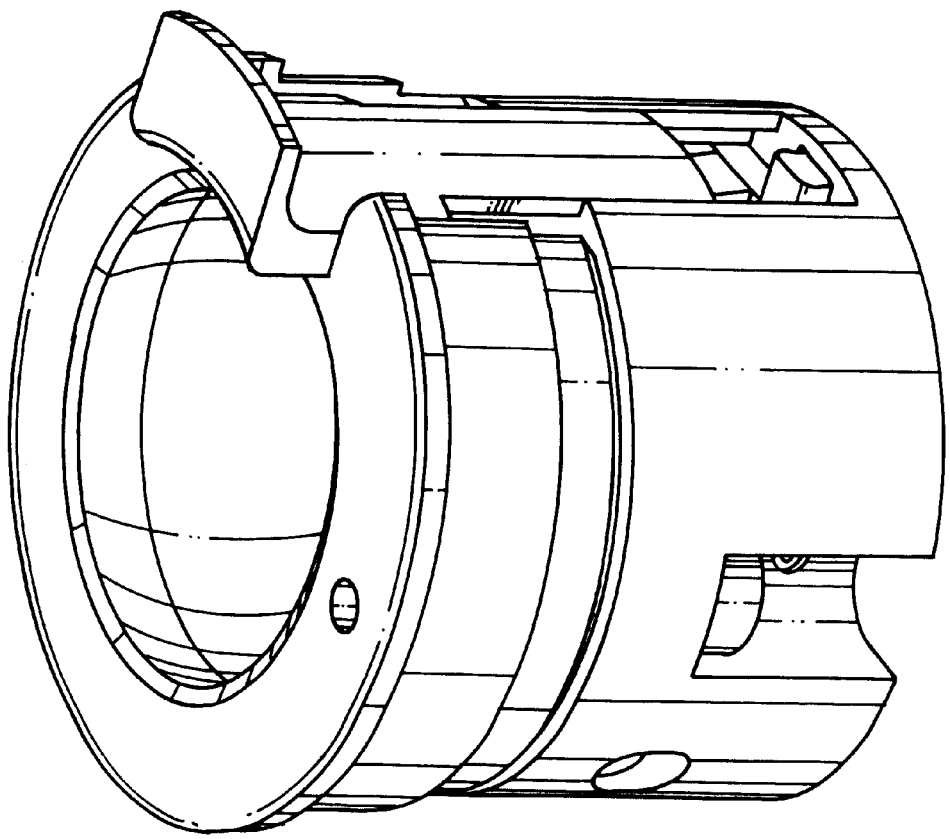
FIGS. 5A and 5B show an alternative form of the overall actuator assembly.
Figure 6B:
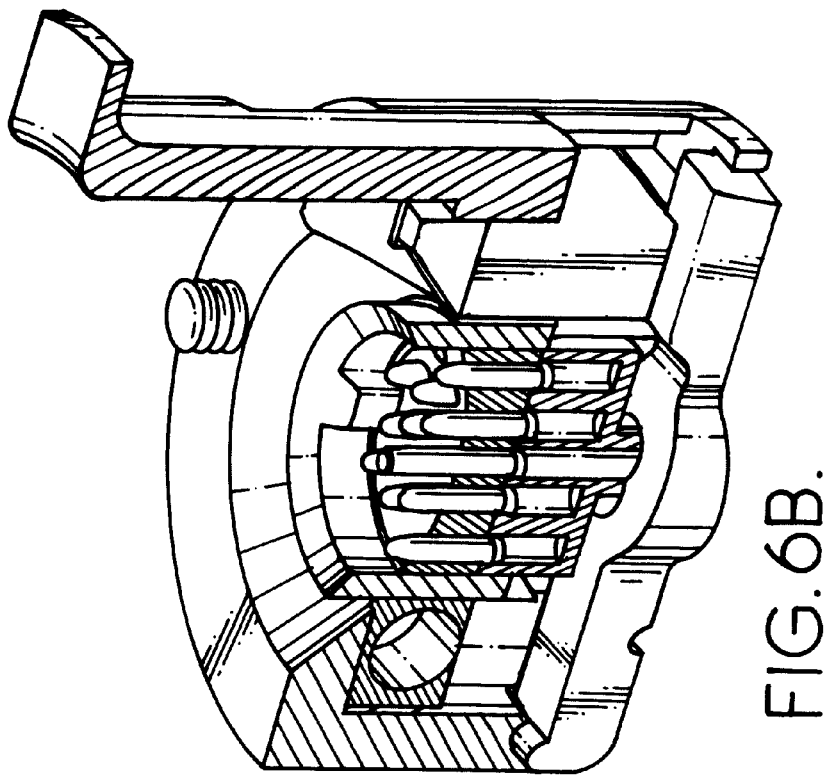
Figure 5B:
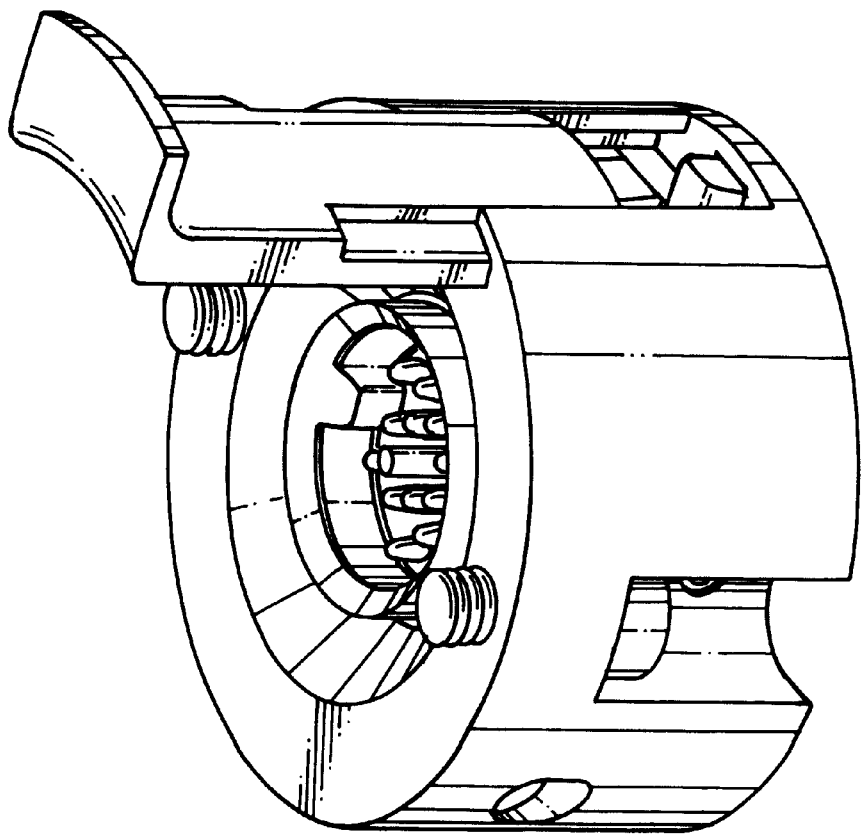
Figure 38A:
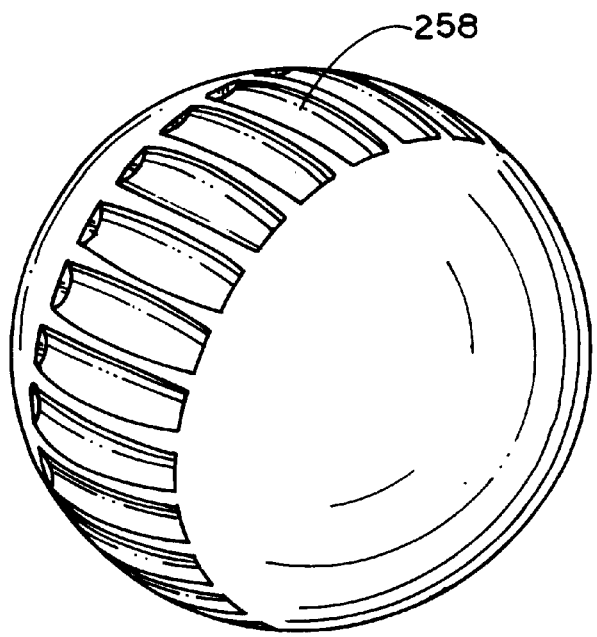
FIGS. 38A and 38B show a uni-directional joint using a row of protuberances.
Figure 38B:
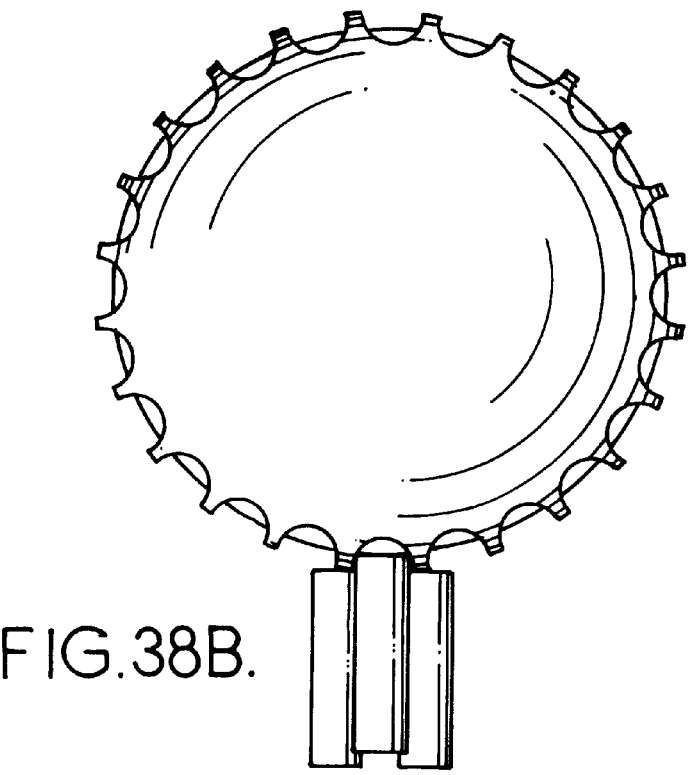

As discussed above, joint mechanism A effectively joins the two parts together and prevents pitch and yaw movements between the joined parts. It is the main object of the present invention to prevent roll between the two parts. Accordingly, the present invention improves joint mechanism A by providing a means on the joint mechanism for mechanically preventing roll movement between the first and second parts. The preferred form of this means is shown in FIG. 3 in which actuator assembly 10 of the present invention includes an actuator top section 12 and an actuator bottom section 14 coupled together by ribs 16 on top 12 slidably received in channels 18 on bottom 14 to slidably connect the top section to the bottom section. Bottom section 14 further includes a bore 20 in which clicker spring 22 is accommodated, and at least one bore 24 spaced from central bore 20. A spring 26 is accommodated in bore 24. Preferably, there are a multiplicity of bores 24, and each will accommodate a spring. In assembly 10, the clicker facilitates stabilizing the joint in the unlocked position and also guarantees smooth clicking transition from one locking position to the next but does not participate in the actual locking of the joint assembly. When shifting and locking the joint in small increments, the clicker pin can be replaced by a locking pin, and a ring-like actuator assembly such as shown in FIGS. 36–38 and discussed below could be used to space the actuator assembly from the protuberances.

Figure 4:
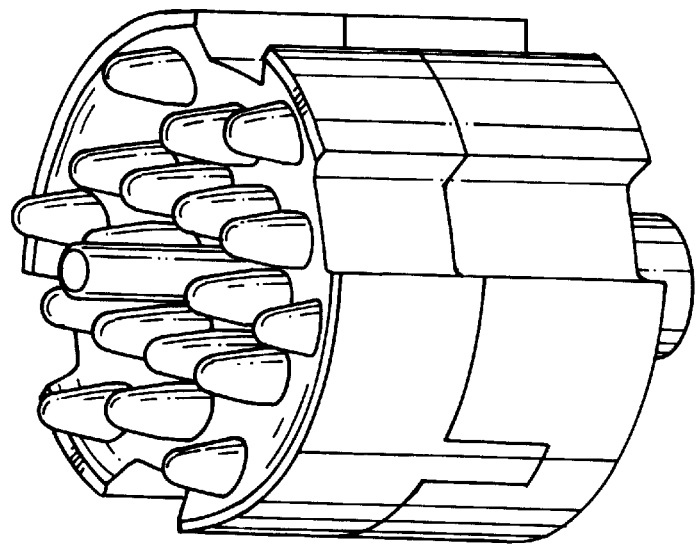
FIG. 4 is an assembled view of the actuator assembly shown in FIG. 3.

Actuator top section 12 includes a central bore 30 and at least one bore 32 spaced from bore 30. As can be seen in FIG. 3, a central actuator pin element 34 is accommodated in bore 30 and a pin element 36 is accommodated in bore 32. The pin elements 34 and 36 are slidably accommodated in the bores 30 and 32 respectively and each has one end 38 and 40 engaging springs 22 and 26 respectively to be urged outwardly of the bores in direction 42 by the springs 22 and 26. Each pin further includes a distal end 44 and 46 respectively which are located in the spaces between protuberances 4 to engage the pins with the protuberances thereby coupling actuator 10 to spherical element 1. Actuator pin 34 can include a concave tip 48 as described in the incorporated patent. It is also noted that, if suitable, each actuator head or a plurality of the actuator heads or pins can include an indent similar to the concave tip 34 just described. As can be seen in FIGS. 3 and 4, the preferred form of the actuator 10 includes a plurality of pin elements 36 whereby a plurality of concavities on spherical member 1 are engaged simultaneously with the concavity accommodating central pin element 34. For purposes of this disclosure, pin 34 will also be referred to as a clicker pin which facilitates smooth readjustments of the joint, or 36L denominating the central pin as a locking pin, and pin 36 will also be referred to as a locking pin.

As can be seen in FIGS. 3, 4 and 8, top portion 12 has an arcuate surface 50 which is shaped to correspond to the shape of surface 3 of member 1 whereby member 1 is securely accommodated against surface 50 when the joint is assembled. Housing H will enclose both members whereby a rounded member or an arcuate adjustable body of which the spherical ball is an example is secured against arcuate surface 50 with pin elements 34L and 36 securely accommodated between associated protuberances to lock the parts together.

As will be understood by one skilled in the art from the teaching of this disclosure, once the spherical element is secured against the surface 50 in and by housing H, the parts will be mechanically secured against pitch, yaw and roll by the engagement of the pin elements and the protuberances. However, once the housing is released so the spherical ball can be moved away from surface 50 far enough so tips 44 and 46 of the pin elements are released from abutting engagement with the protuberances, the spherical ball element can be moved relative to surface 50 whereby the relative orientation of the parts can be changed in any plane. The relative movement between the two parts can be incremental as measured by the pin elements 34 and 36 moving over the protuberances 4 so the movement can be measured both audibly by clicking sounds and tactilly by the feel of the pin elements moving over the protuberances. To achieve the tactile feel of the joint during shifting, the actuator heads or pin elements may slightly graze the protuberances, but may also be totally spaced from the arcuate adjustable body of the joint if desired. The great number of pin elements and protuberances permits a wide range of relative positions between the two parts, yet will provide a great number of fine incremental adjustments to such movements. At any chosen position, the spaced apart locations of the pin elements mechanically prevents roll motions between the parts as well as assists in the prevention of pitch and/or yaw motions as well.

Figure 10:
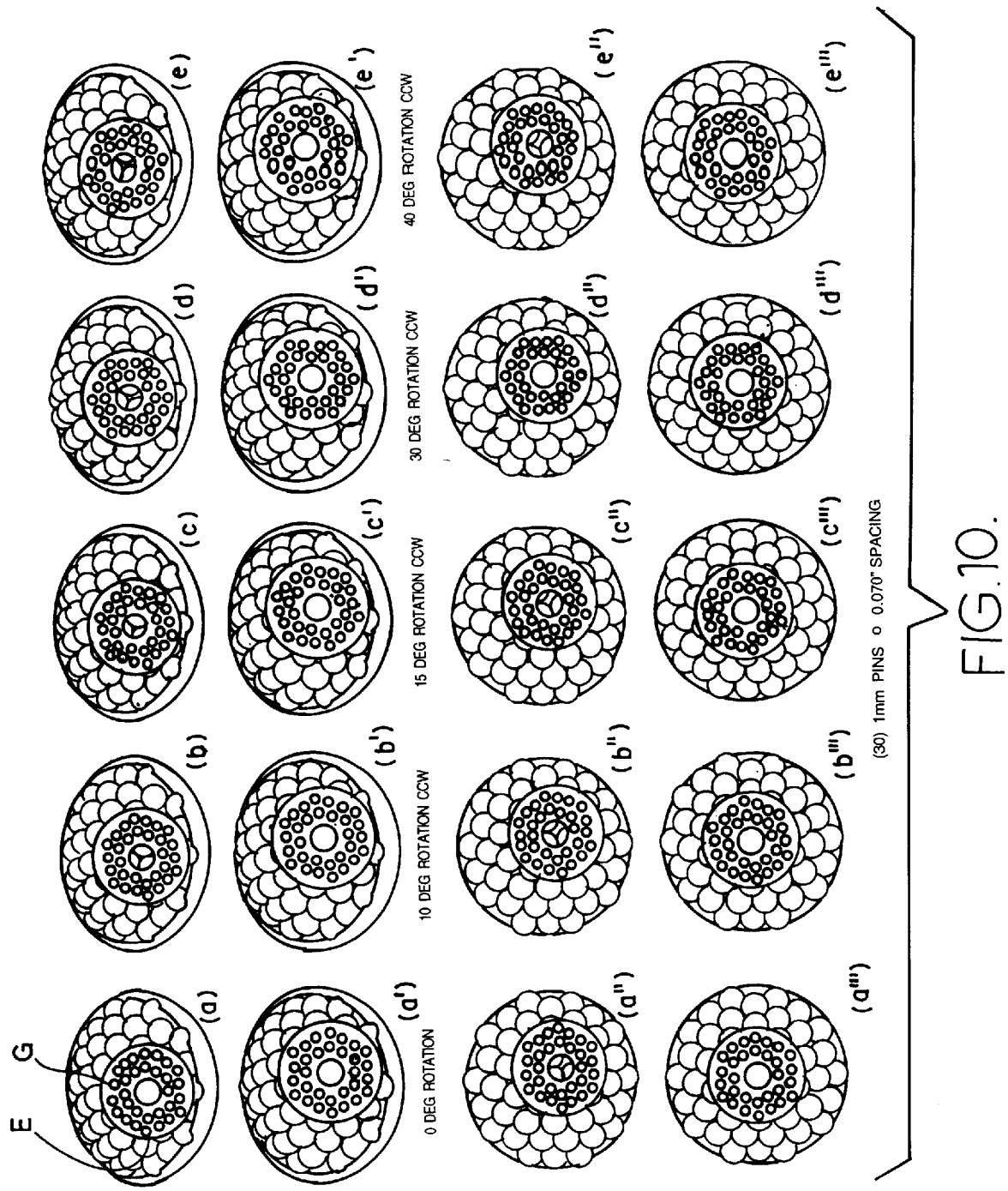
FIG. 10 are schematic representations showing various pin engagement patterns for the actuator assembly of the present invention.

At any orientation, several pins will engage between protuberances in a manner that securely locks the two parts together. Several engagement patterns are shown in FIG. 10, with the filled-in circles E indicating fully engaged pins, and the empty circles G indicating pins that are engaged with protuberances but not fully engaged on all sides by protuberances.

Figure 11:
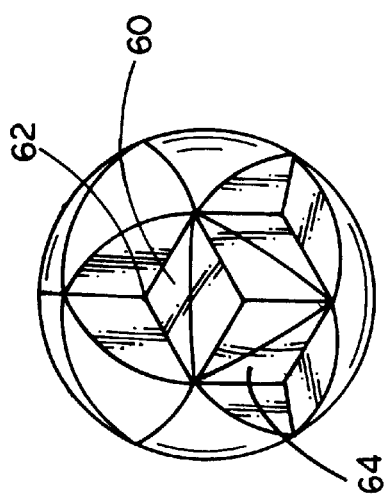
FIG. 11 shows a protuberance pattern that can be incorporated in the actuator assembly of the present invention.

The protuberance patterns a and b shown in FIG. 1 are just two choices that can be made. Other patterns are also possible, such as the icosahderon pattern d shown in FIG. 11.

Pattern d includes adjacent spherical triangular walls 60 which extend into the spherical member and intersect at an nadir point 62 and which intersect with one another at bases 64 on the outer surface of the spherical member. Pin element tips 44 and 46 are received in the openings defined between walls 60. Other patterns can also be used as will occur to one skilled in the art based on the teaching of the present disclosure.

Figure 13C:
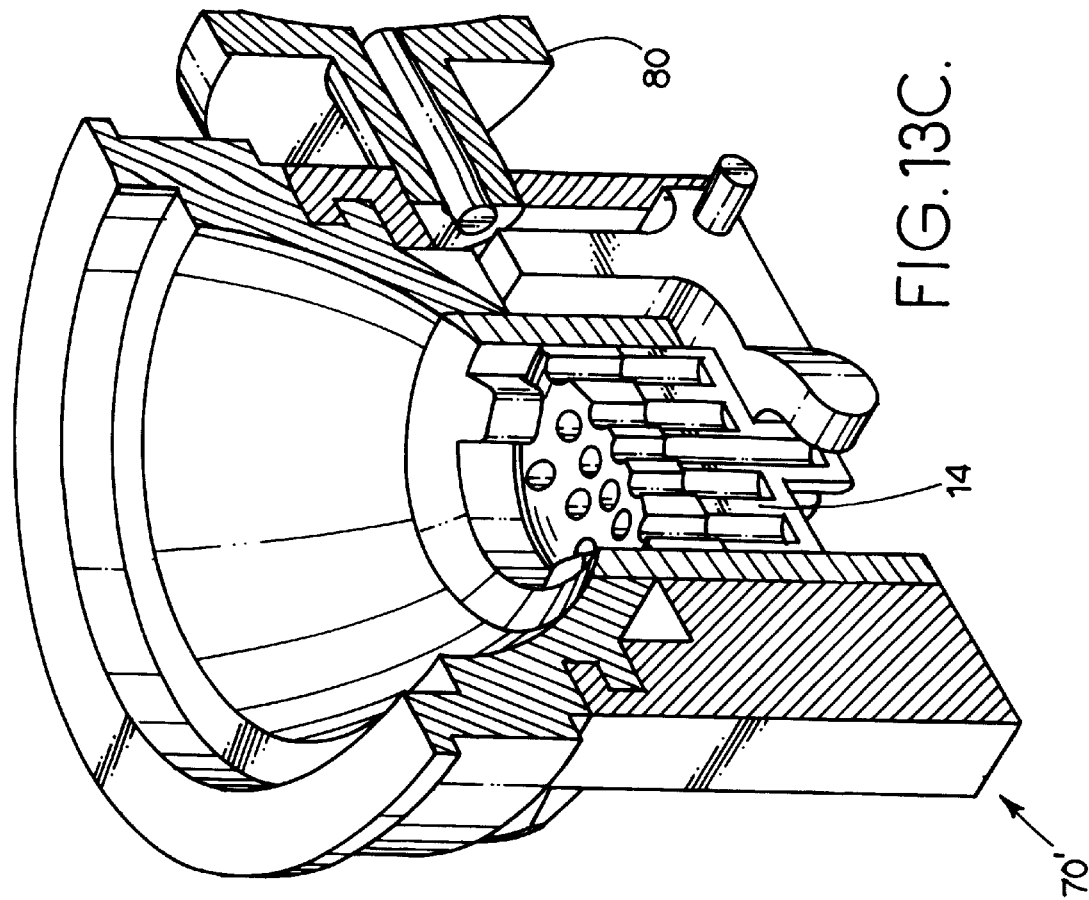
FIG. 13C is a cutaway perspective view of one of the assembled joint mechanisms.
Figure 12:
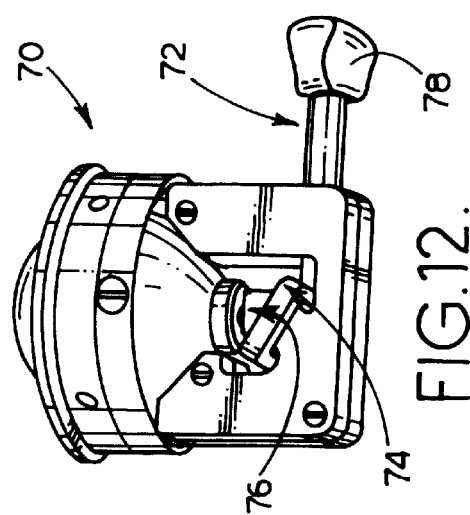
FIG. 12 is a bottom perspective view of one of the assembled joint mechanisms of the present invention.
Figure 13A:
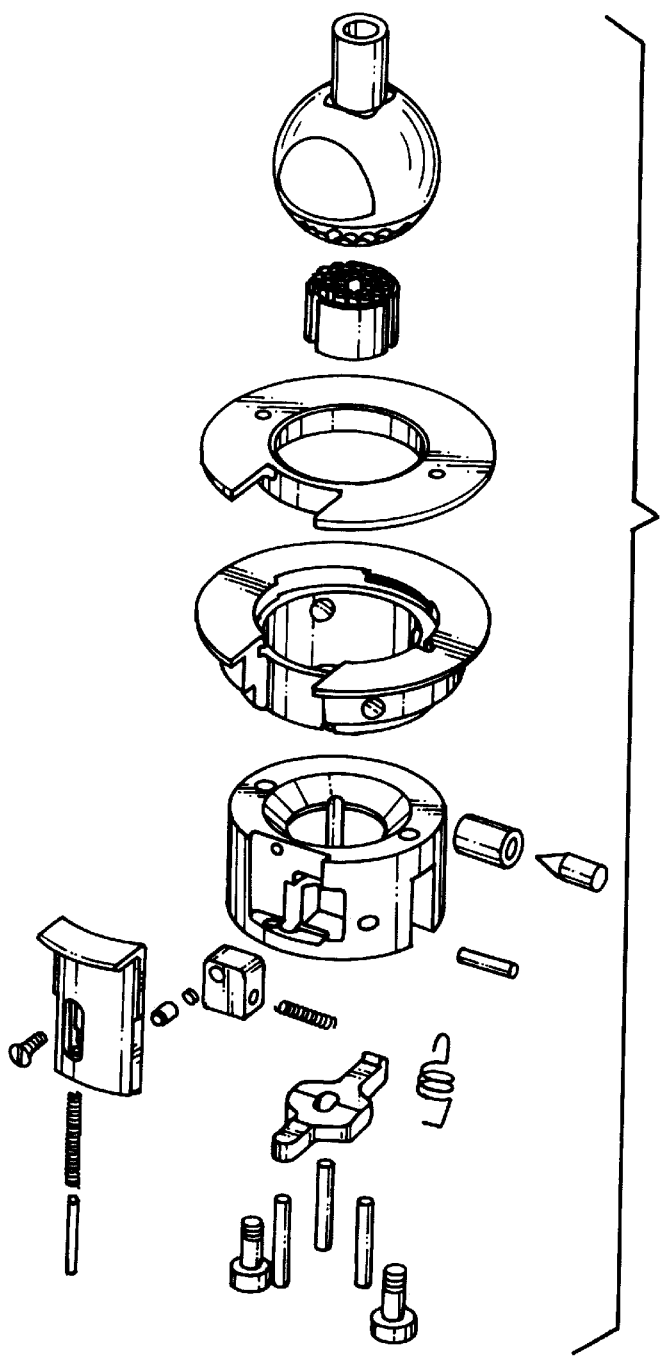
FIG. 13A is an exploded perspective view of a mechanism.
Figure 13B:
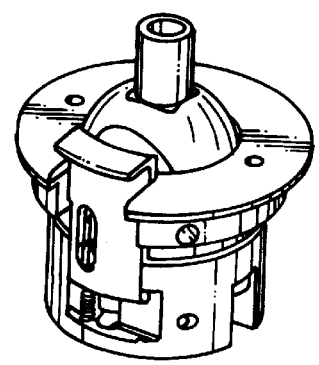
FIG. 13B is an assembled view of the mechanism.
Figure 14:
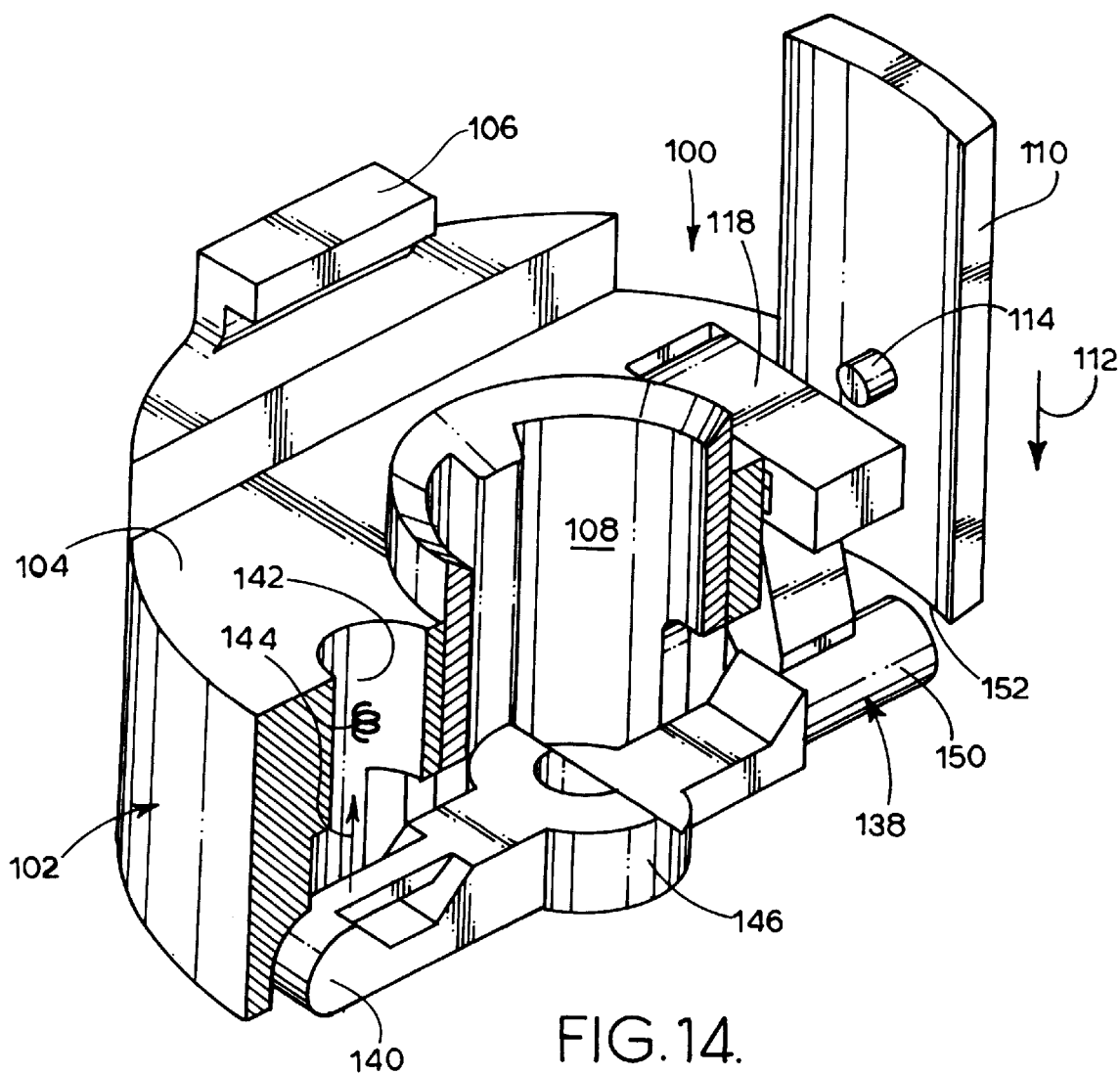
FIG. 14 is a cutaway view showing one form of a mechanism for opening and closing the assembly.

Other assembled joint mechanisms are shown in FIGS. 12 and 13 along with means for operating that mechanism to engage and disengage the pin elements and the protuberances. As shown in FIG. 12, overall assembly 70 includes an operating handle 72 which is spring biased to have its proximal end 74 urged upwardly in direction 76. Proximal end 74 engages bottom 14 to urge it towards rounded member 1 to engage the pins with the protuberances as discussed above. When distal end 78 is operated, the pins are moved away from the protuberances to disengage the mechanism. Another form of operating mechanism is illustrated in FIG. 13C as assembly 70', and includes a handle 80 which is moved to move bottom 14 away from rounded member 1 and thereby disengage the pins from the protuberances.

Yet another form of the operating mechanism is shown in FIGS. 14–18F. As shown, operating mechanism 100 includes a housing 102 with a top web 104 which includes tabs, such as tab 106 which engage the housing of the assembly 10 when it is received in well 108. Operation of mechanism 100 opens and closes the assembly by moving that assembly so the pins engage the protuberances as discussed above, and by moving the pins away from the protuberances to disengage the assembly 10.

Figure 15:
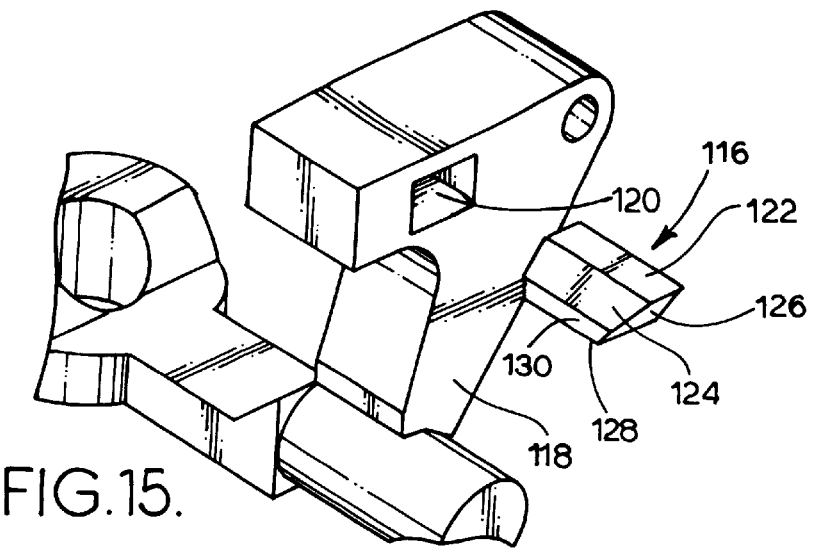
FIG. 15 is an enlarged view of a portion of the mechanism shown in FIG. 14.
Figure 16:
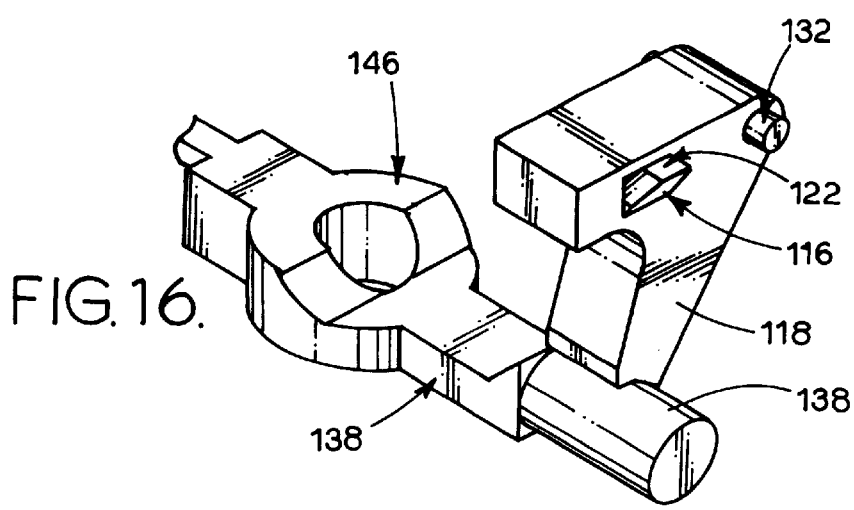
FIG. 16 shows the portion of the mechanism shown in FIG. 15 in an assembled condition and in a link engaging configuration.
Figure 17:
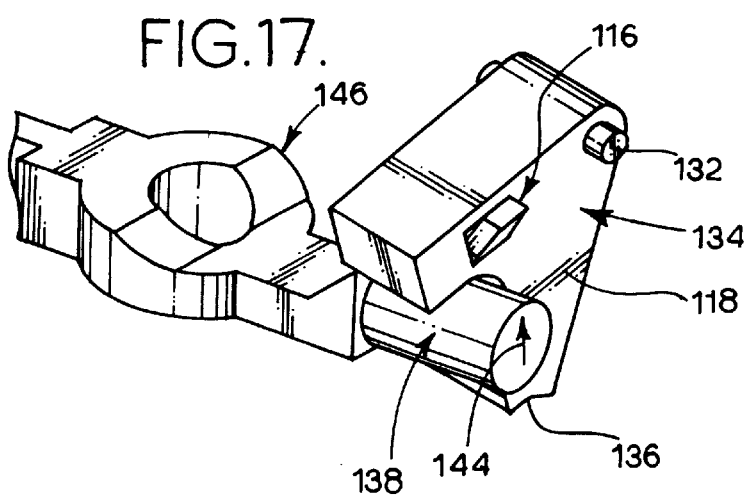
FIG. 17 shows the FIG. 16 portion of the mechanism in a link freeing configuration.
Figure 19B:
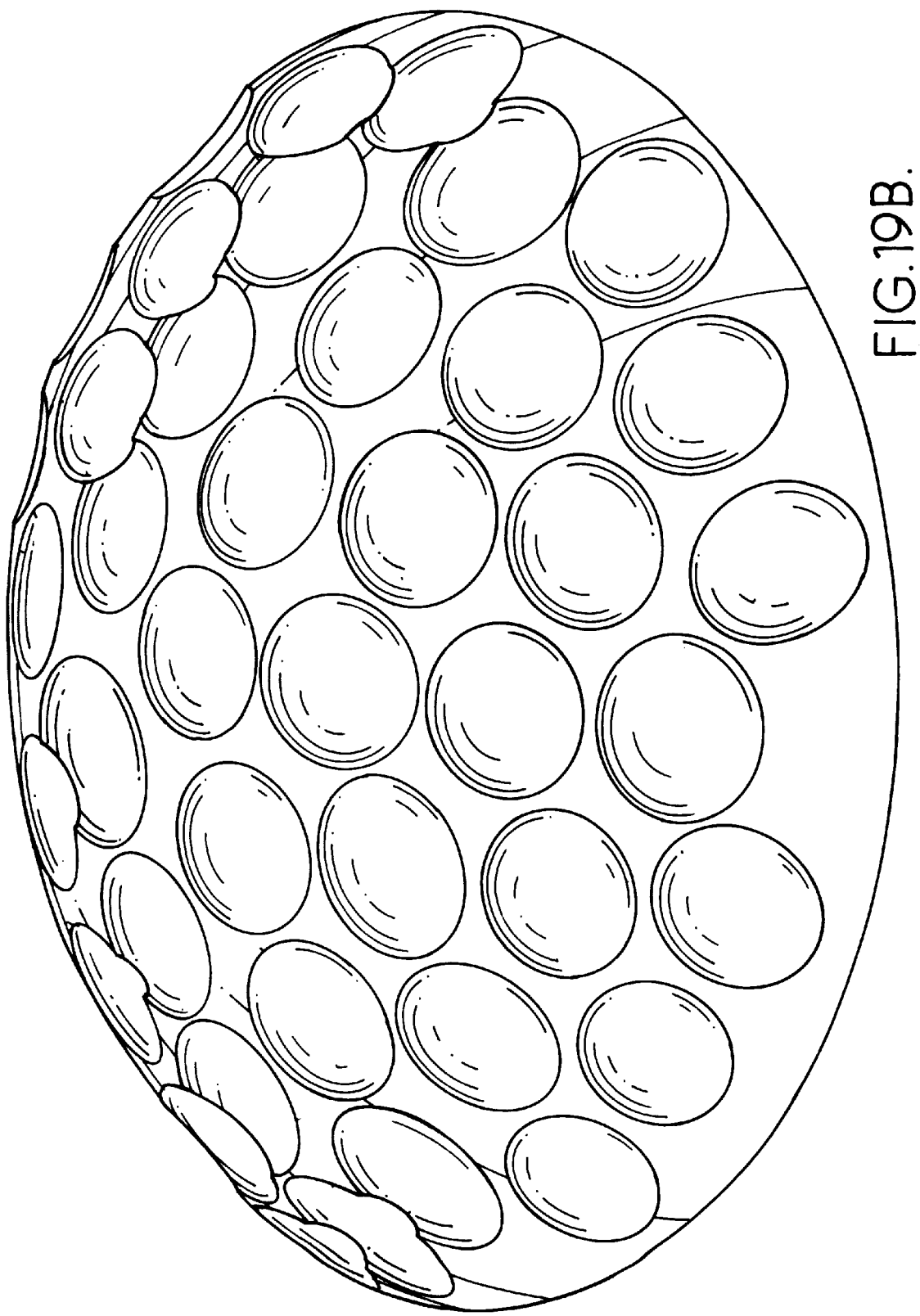
Figure 19D:
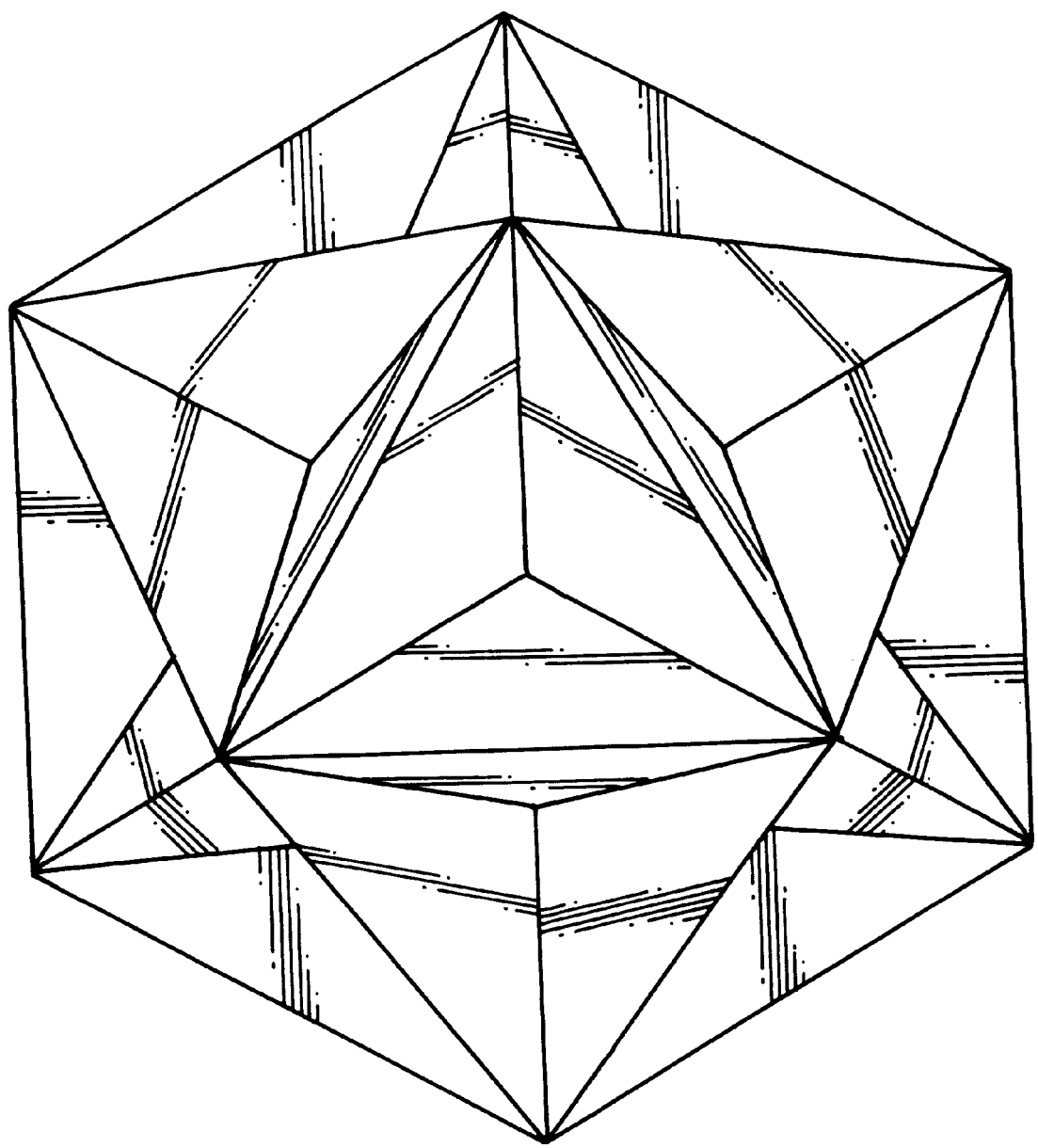

Movement of the assembly portions is accomplished by mechanism 100 by depressing a button 110 in direction 112. Button 110 includes a pin 114 which engages a latch pin 116 on a lever arm 118. As shown in FIGS. 15 and 16, pin 116 is received in a slot 120 in lever 118 and is spring biased outward of the slot. Pin 116 has a top surface 122, a sloping side surface 124 and a sloping end surface 126 with a bottom surface 128 and a lower surface 130 completing the outer perimeter of the pin. Pin 116 is located near one end of the lever 118 and a pivot pin 132 is located on another end of lever 118 with lever 118 pivoting around pivot pin 132. A spring (not shown) biases lever 118 in direction 134. A lower end 136 of lever 118 is arcuate and engages a spur link 138 when it is desired to hold the pins of the assembly 10 away from engagement with the protuberances of the assembly. Spur link 138 is pivotally connected to housing 102 adjacent to end 140 of the spur link and a spring 141 located in spring well 142 in housing 102 and pulls spur link 138 upwardly in direction 144. Spur link 138 includes a section 146 which engages assembly 10 to move that assembly in direction 144 so the pins engage the protuberances under the influence of the spring 141.

When it is desired to release the pins from the protuberances, button 110 is depressed in direction 112. As indicated in FIGS. 18A–18F, as button 110 moves in direction 112, lever 118 pivots about pin 132 in a counterclockwise direction and pin 114 slides along surface 124 of pin 116. The arcuate end 136 is moved off of arcuate end 150 of spur link 138 and spring 141 causes the spur link to move upwardly in direction 144 once end 136 of pin lever 118 moves off of end 150 of link 138 as indicated in FIG. 18B. At this point, the joint is locked (snaps shut). Taking a user's finger off the button allows the spring loaded button to return to its starting position. Further downward movement of button 110 causes pin 114 to slide downward on surface 124 without further pivoting movement of lever 118. Bottom edge 152 of button 110 engages end 150 of spur link 138, and further downward movement of the button moves spur link 138 downwardly in the direction opposite to direction 144. Such movement will move the pins of assembly 10 away from the protuberances thereby unlocking the joint.

Eventually, end 150 of spur link 138 will be moved downward far enough so that end will re-engage with end 136 of lever 118 as indicated in FIG. 18F. Button 110 can be moved either manually or by a spring back into the FIG. 18A position while end 150 remains engaged with end 136 thereby keeping the pins of the assembly spaced from the protuberances.

As discussed above, any protuberance pattern is suitable for use on assembly 10 just so the conditions set forth hereinabove are satisfied. Several protuberance patterns are illustrated in FIGS. 19A–19E. As discussed above, the protuberance patterns can include spaced, interconnected, honeycomb shaped, bridged, converging at one or more points, or can be totally separate. The protuberances can be wedge shaped, conical, pyramidal, triangular, polygonal, elongated or can be mixed shapes. The protuberances can be of various sizes and heights as well. It is also noted that the tip 44 as well as other tips can, in some conditions, touch the surface of the rounded member. Since some protuberance patterns may be very complex, the number of actuator heads or pins 32 can vary. The individual heads of the pins can be in close proximity to each other or spaced apart as necessary to best penetrate and lock onto a given protuberance pattern. Shape and size of the actuator heads 44 and/or 46 is determined by the size and shape and pattern of the concavities.

It is also noted that while one assembly has been described, more than one single headed or multi-headed assembly can be used on a single joint without departing from the scope of the present disclosure.

Figure 20:
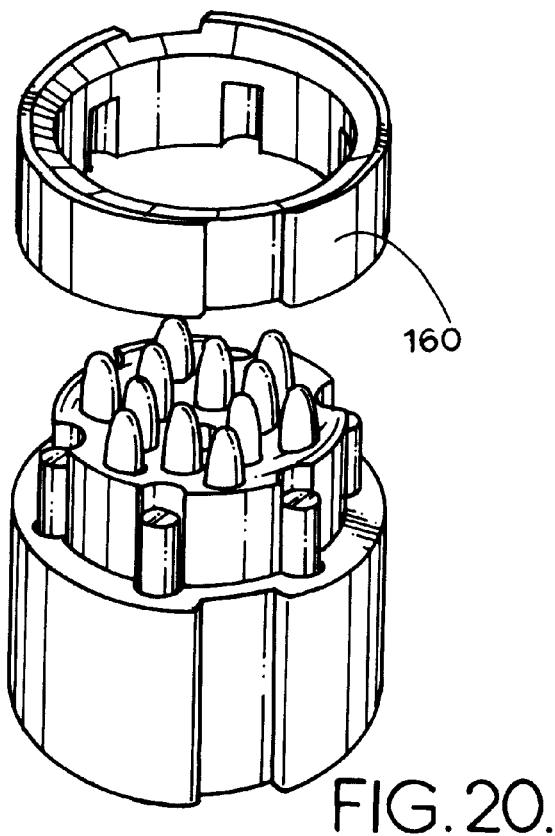
FIG. 20 is an exploded assembled view of a varient of the proposed actuator mechanism.
Figure 21:
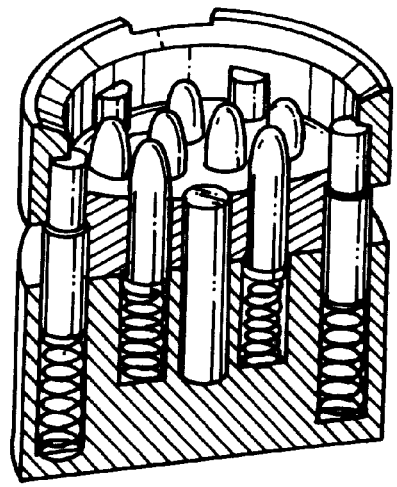
FIG. 21 is a section view of the mechanism shown in FIG. 20.
Figure 22:
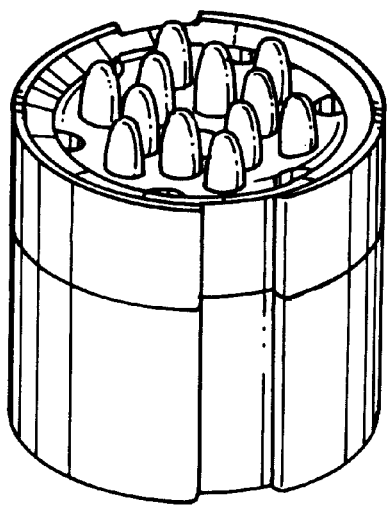
FIG. 22 is an assembled view in an engaging configuration.
Figure 23:
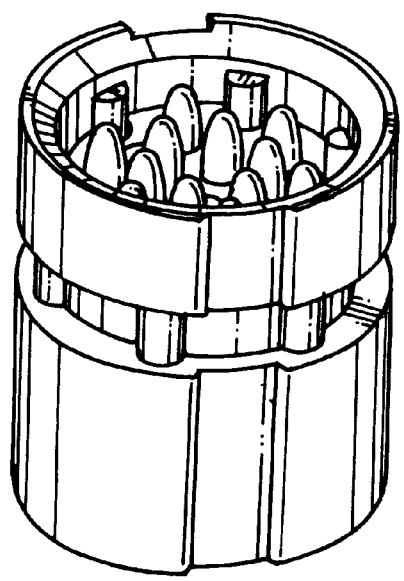
FIG. 23 is an assembled view in a disengaging configuration.
Figure 24:
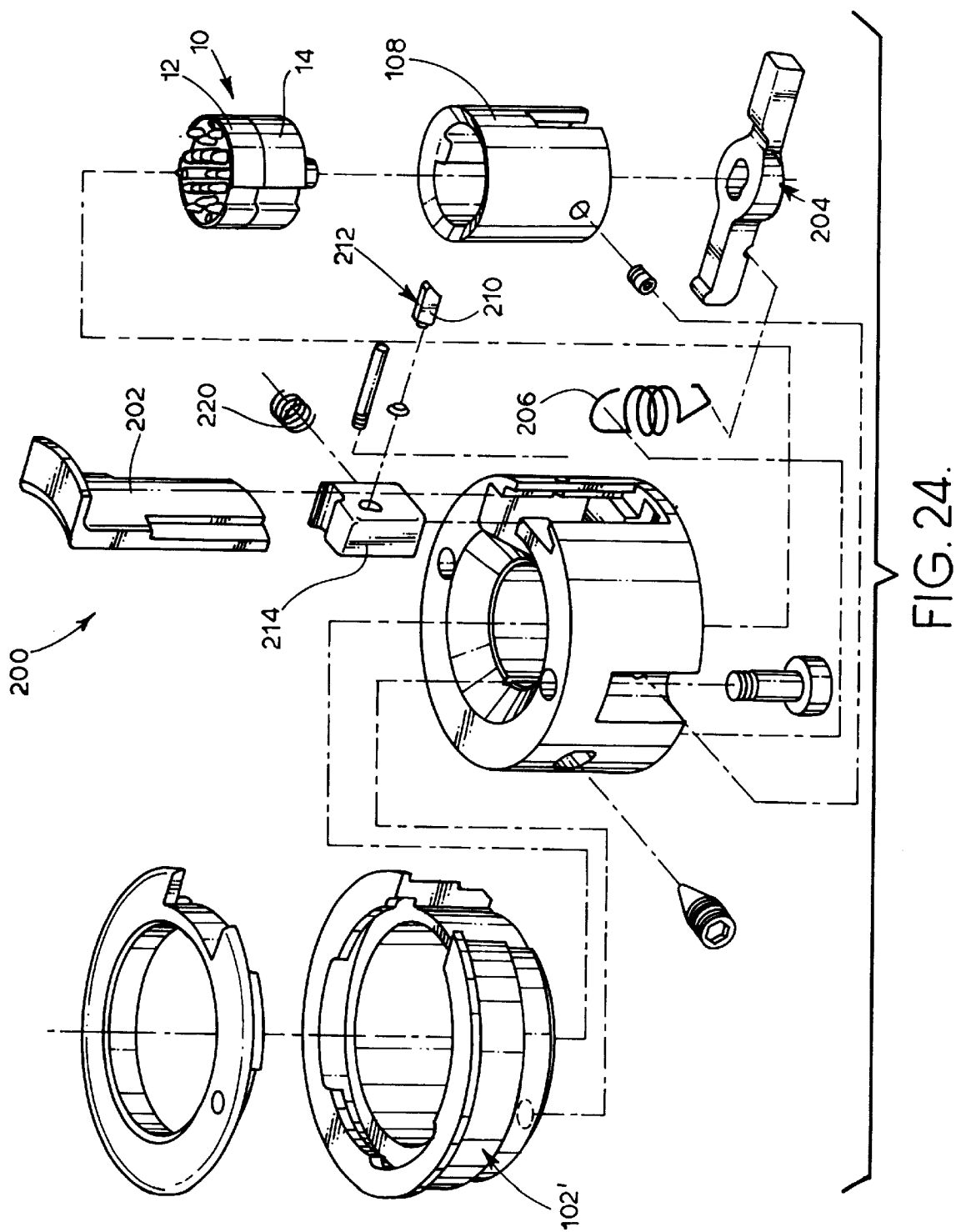
FIG. 24 is an exploded view of the overall mechanism.
Figure 25:
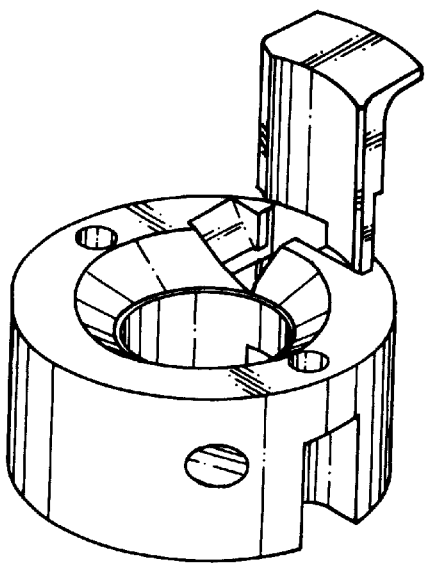
FIGS. 25–30 show various elements of the overall mechanism shown in FIG. 24.
Figure 26:
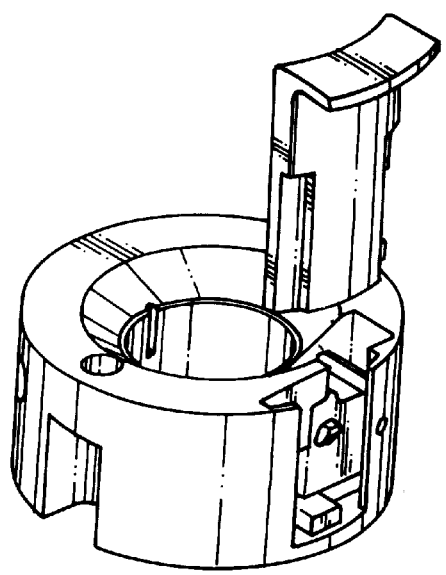
Figure 27:
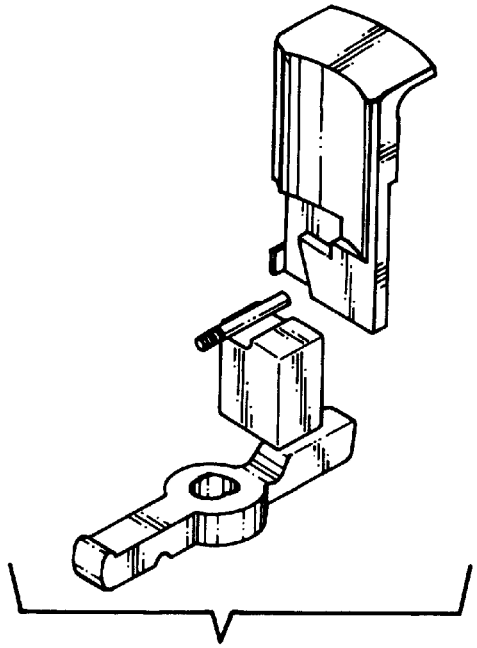
Figure 28:
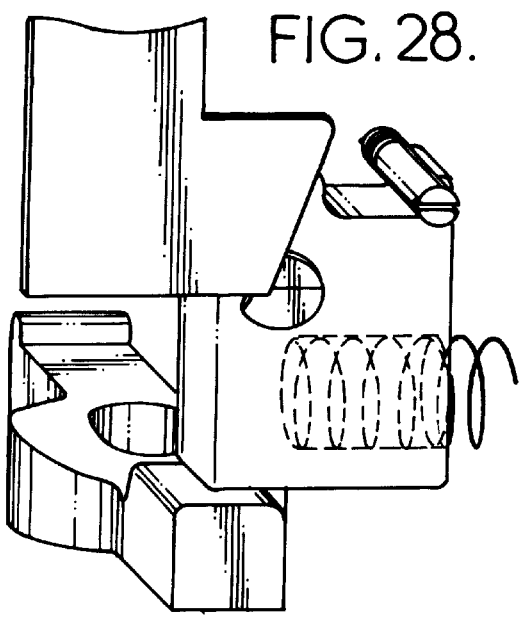
Figure 29:
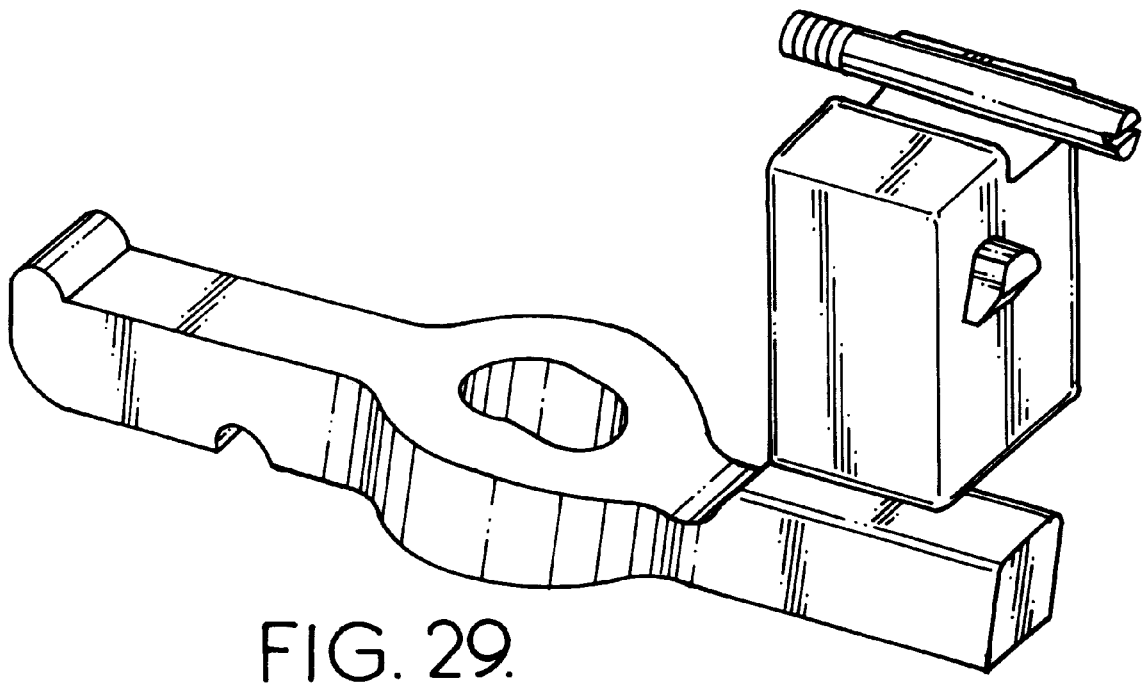
Figure 30:
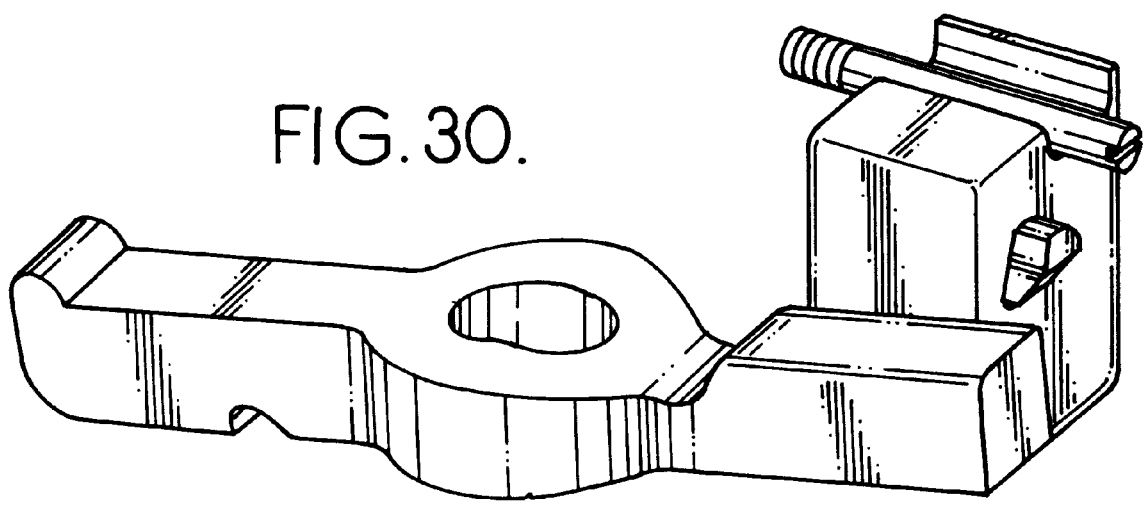

FIG. 3 illustrates a single central clicker pin; whereas, FIG. 20 illustrates a multiplicity of locking pins and no clicker pin. A ring element 160 is shown and engages the spherical element to move that element as discussed above to engage (FIG. 22) and disengage (FIGS. 21 and 23) the pins and protuberances. Movement of ring 160 is achieved by a mechanism such as shown in FIGS. 14–18F and described above. The ring also prevents the jointed head from flopping around in an unlocked position to ensure smooth operation of the assembly. The smooth operation also allows minute angular readjustments to the joint while providing unlimited locking positions. In a locked mode, the ring is pressed down on the lower actuator body thereby allowing the locking pins to engage into the protuberance patterns of the rounded member.

It is understood that while certain forms of the present invention have been illustrated and described herein, it is not to be limited to the specific forms or arrangements of parts described and shown. For example, as shown in FIG. 3A, the spring elements 22 and 26 used to bias elements 34 and 36 could be replaced by electro-mechanical elements such as solenoid-operated elements without departing from the scope of the present invention. Still further, various overall mechanisms can be used to operate the actuator assembly 10.

Figure 32A:
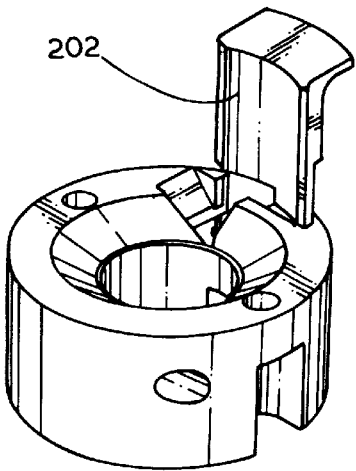
FIGS. 32A–32D illustrate operation of the FIG. 24 mechanism.
Figure 32B:
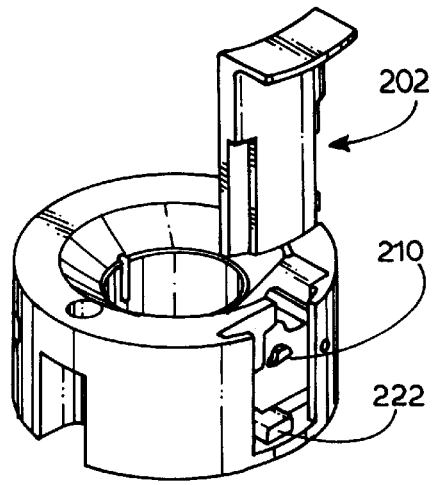
Figure 32C:
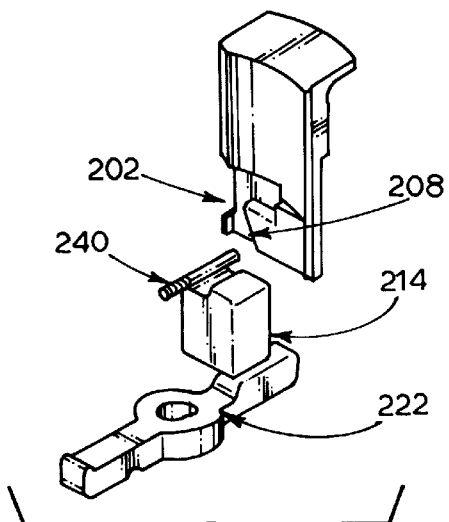
Figure 32D:
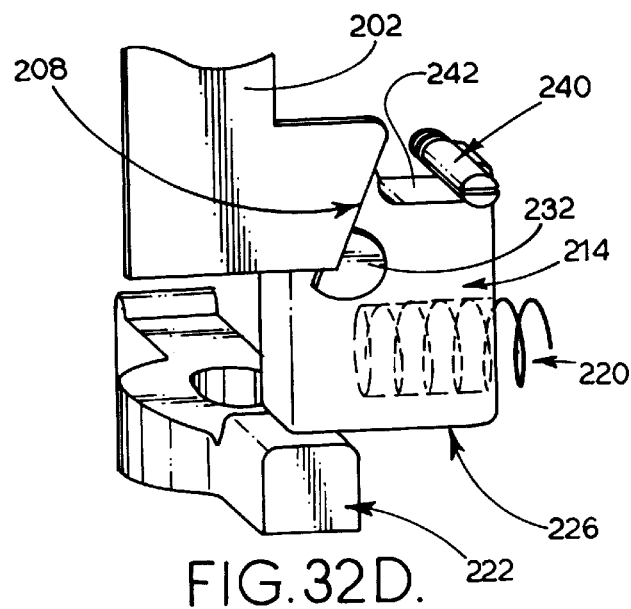

For example, FIGS. 24–31E illustrate an overall mechanism 200 in which a button element 202 operates a lever element 204 to move mechanism 10 within well 108 as discussed above. Referring to FIGS. 31A–31E in conjunction with FIGS. 24–30 and 32A–32D, it can be understood that depressing button element 202 downward against the bias of spring 206 forces surface 208 against surface 210 of door latch element 212 thereby forcing locking link 214 toward the right in FIG. 31A against the bias of spring 220. Once the link 214 is moved far enough, it snaps behind spur link 222 as shown in FIG. 31B, and spring 206 causes the button element to return to its up position shown in FIG. 31C with spur link 222 abutting front surface 224 of spur link 222. To release the mechanism, button 202 is again depressed against the bias of spring 206 until the button moves the spur link down beneath surface 226 of link 214. At that time, as shown in FIG. 31D, spring 220 moves link 214 to the left of FIG. 31D. Since door latch element 212 is positioned above ledge 230 of button 202, link 214 is free to move to the left of FIG. 31C into the position shown in FIG. 31D. As can be seen in FIG. 32D, latch element 212 is shaped in the form of a door latch element to have an angled surface 232. Angled surface 232 engages ledge 230 and the spring force exerted by spring 206 is sufficient to move ledge 230 past the angled surface 232 whereby button element 202 can move from the position shown in FIG. 31D to the position shown in FIG. 31E. Continued movement of button element 202 under the influence of spring 206 causes the button element to re-establish the position shown in FIG. 31A to begin the cycle again. Shaft element 240 engages surface 242 of link 214 to guide and control movement of the link. Assembly 10 is coupled to lever element 204 to be moved in a manner that will operate the pin elements as discussed above.

Figure 33:
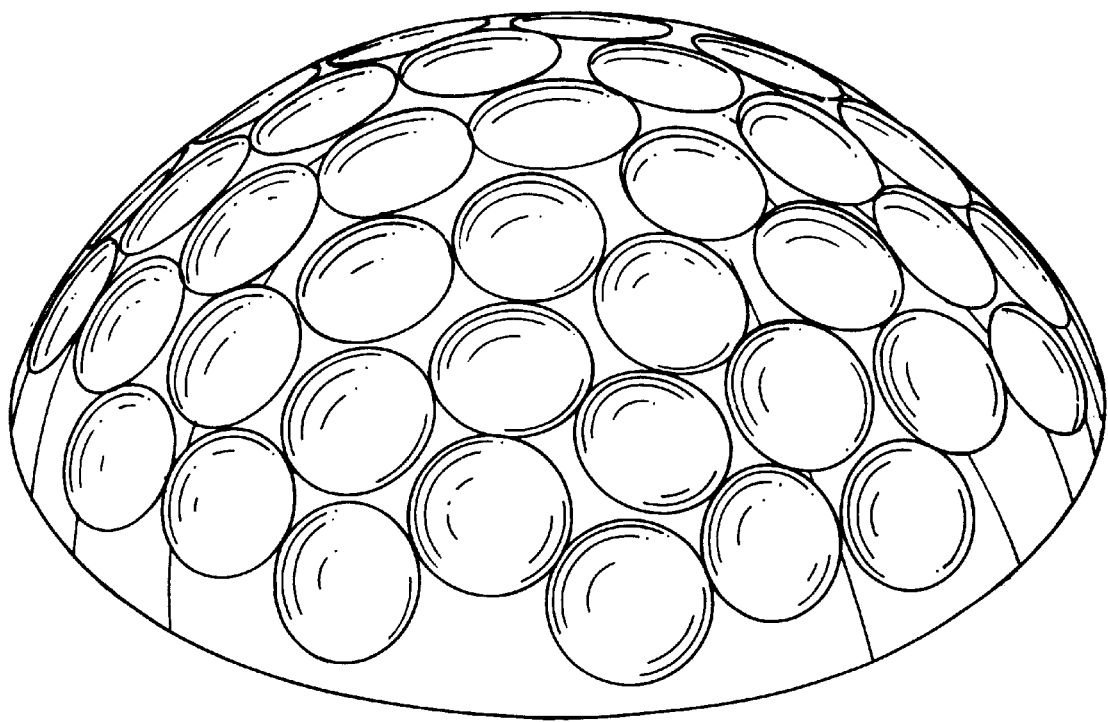
FIG. 33 shows yet another protuberance pattern.
Figure 34:
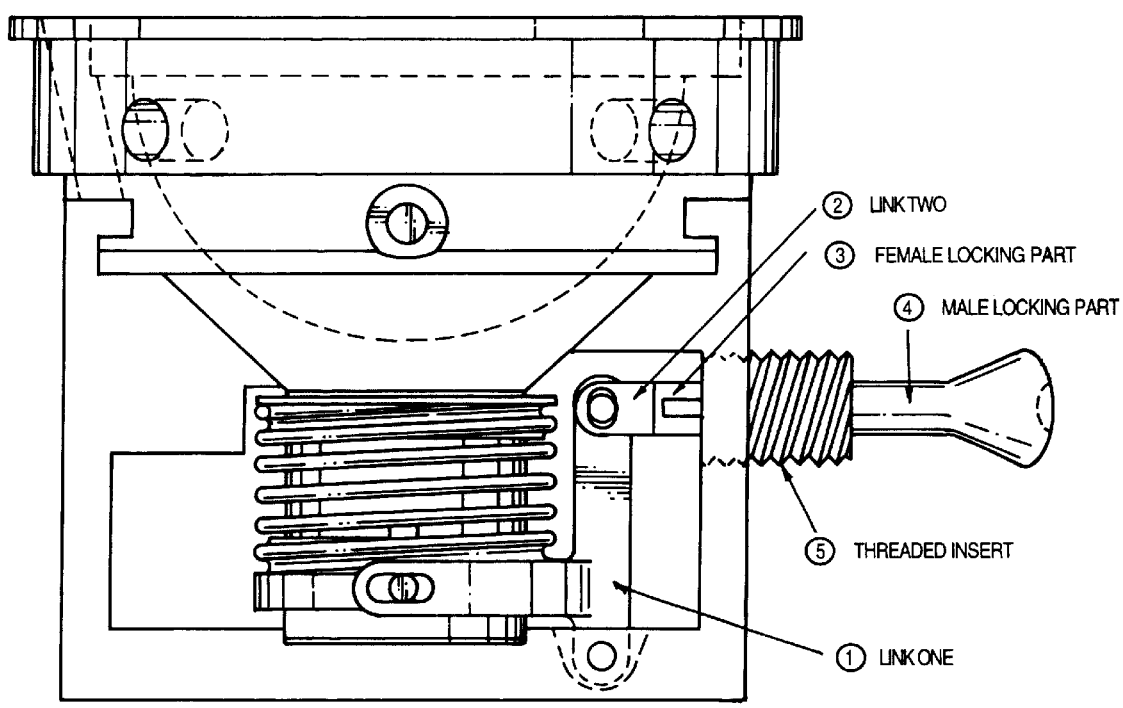
FIGS. 34 and 35 show yet another overall mechanism.
Figure 35:
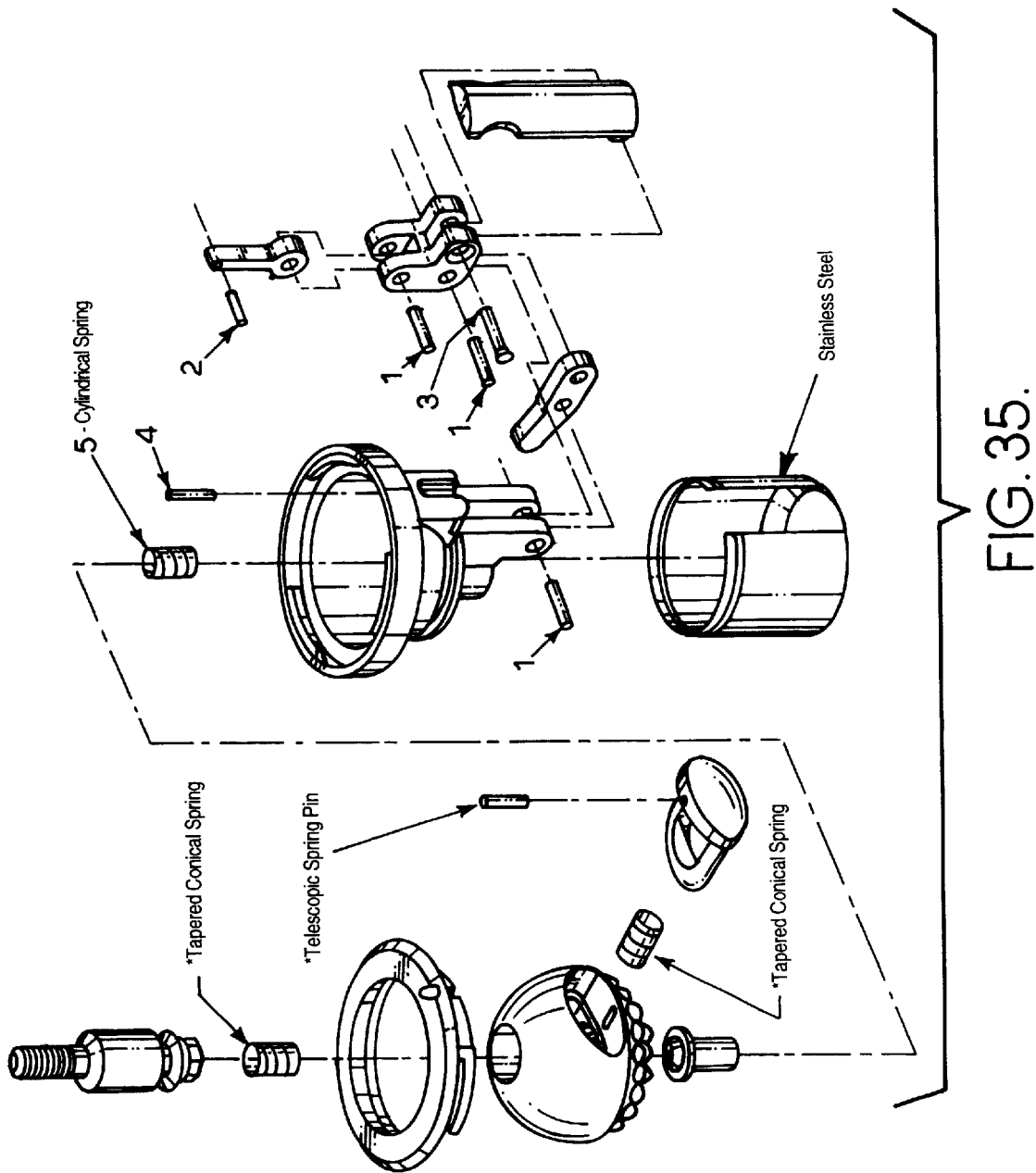

Other forms of the overall operating mechanism are shown in FIGS. 34 and 35. One skilled in the art will be able to understand the operation of these mechanisms from the figures as well as the foregoing teaching. Therefore, the operation of these mechanisms will not be detailed here. FIGS. 36A–37B illustrate yet another form of the invention in which a single row of protuberances, such as protuberances 250 in FIG. 36A engage adjacent rows of pins, such as pins 252, 254 and 256 to achieve the above-discussed results. A single row of protuberances such as protuberance 258 can also be used for a uni-directional joint. Yet another form of protuberance pattern is shown in FIG. 33.

What is claimed is:

1. An angularly adjustable, releasably lockable joint mechanism for rigidly joining first and second parts at a selected orientation: comprising a first member with a plurality of concavities defined on its surface and being secured to the first part, a second member accommodating the first member, at least one disengageable actuator extending through the second member and having a tip and being operative to advance the tip to lock up with the first member by being located in at least one concavity or to retract the tip to disengage it from the first member, the actuator being connected with the second part, and means for holding the parts, first member, the second member, and actuator together, said means being operative to allow the parts to change relative orientation when the actuator is retracted while the first member and the second member remain engaged with each other, the first member having a plurality of patterns of protuberances covering at least part of its surface, the protuberances of each pattern forming a concavity therebetween, the protuberances, the tip of said actuator and patterns being dimensioned relative to each other so that the tip of said actuator can be located in the concavity of each pattern and contact the protuberances of the pattern adjacent thereto while remaining spaced from the surface of the first member;

said actuator having a base end and a spring engaging the base end of said actuator and biasing the tip end of the actuator into engagement with the protuberances of the first member;

a locking pin on the second member and spaced from the tip of the disengageable actuator, said locking pin having a tip end and a base end and a spring engaging the base end of the locking pin and biasing the tip end of the locking pin into engagement with protuberances on the first member at a location spaced from the location whereat the tip of the disengageable actuator engages protuberances whereby roll movement between the first and second parts is prevented.

2. The joint mechanism defined in claim 1 further including a plurality of locking pins.

3. The joint mechanism defined in claim 2 further including a plurality of springs with each spring engaging one locking pin of said plurality of locking pins.

4. The joint mechanism defined in claim 3 wherein the second member includes a plurality of bores and at least two of said locking pins are each located in a bore.

5. The joint mechanism defined in claim 3 further including a housing enclosing both the first and second members.

6. The joint mechanism defined in claim 3 wherein the second member includes an arcuate surface through which said locking pins extend.

7. The joint mechanism defined in claim 3 wherein the clicker pin is positioned centrally of said plurality of locking pins.

8. The joint mechanism defined in claim 1 further comprising protuberance patterns which are derived from icosahedrons.

9. The joint mechanism defined in claim 1 further comprising protuberance patterns which are derived from polyhedrons.

10. An angularly adjustable, releasably lockable joint mechanism for rigidly joining first and second parts at a selected orientation: comprising a first member with a plurality of concavities defined on its surface and being secured to the first part, a second member accommodating the first member, at least one disengageable actuator extending through the second member and having a tip and being operative to advance the tip to lock up with the first member by being located in at least one concavity or to retract the tip to disengage it from the first member, the actuator being connected with the second part, and means for holding the parts, first member, the second member, and actuator together, said means being operative to allow the parts to change relative orientation when the actuator is retracted while the first member and the second member remain engaged with each other, the first member having a plurality of patterns of protuberances covering at least part of its surface, the protuberances of each pattern forming a concavity therebetween, the protuberances, actuator tip and patterns being dimensioned relative to each other so that the tip can be located in the concavity of each pattern and contact the protuberances of the pattern adjacent thereto while remaining spaced from the surface of the first member;

said actuator having a base end and an electro-mechanical element engaging the base end of said actuator and biasing the tip end of said actuator into engagement with the protuberances of the first member;

a locking pin on the second member and spaced from the tip of said actuator, said locking pin having a tip end and a base end and an electro-mechanical element engaging the base end of the locking end and biasing the tip end of the locking pin into engagement with protuberances on the first member at a location spaced from the location whereat the tip of the disengageable actuator pin engages protuberances whereby roll movement between the first and second parts is prevented.

11. The joint mechanism defined in claim 10 wherein said electro-mechanical element includes a solenoid operated element.

12. An angularly adjustable, releasably lockable joint mechanism for rigidly joining first and second parts at a selected orientation comprising: a first part a second part, said first and second parts being movable with respect to each other in a pitch plane, and in a roll plane and in a yaw plane; a first member with a plurality of concavities defined on its surface and being secured to the first part, a second member accommodating the first member, at least one disengageable actuator extending through the second member and having a tip and being operative to advance the tip to lock up with the first member by being located in at least one concavity or to retract the tip to disengage it from the first member, the actuator being connected with the second part, and means for holding the parts, first member, the second member, and actuator together, said means being operative to allow the parts to change relative orientation when the actuator head is retracted while the first member and the second member remain engaged with each other, the first member having a plurality of patterns of protuberances covering at least part of its surface, the protuberances of each pattern forming a concavity therebetween, the protuberances, actuator tip and patterns being dimensioned relative to each other so that the tip can be located in the concavity of each pattern and contact the protuberances of the pattern adjacent thereto;

a locking pin on the second member and spaced from the tip of the disengageable actuator, said locking pin having a tip end and a base end and a spring engaging the base end of the locking pin and biasing the tip end of the locking pin independently of said actuator toward engagement with protuberances on the first member at a location spaced from the location whereat the tip of the disengageable actuator pin engages protuberances whereby roll movement between the first and second parts is prevented.

13. The joint mechanism defined in claim 12 further including a ring element connected to said first member.

14. The joint mechanism defined in claim 12 wherein at least one concavity is elongate.

* * * * *